(12) United States Patent
Takehana et al.

(10) Patent No.: US 8,716,435 B2
(45) Date of Patent: May 6, 2014

(54) MULTIBRANCHED POLYOXYALKYLENE COMPOUND AND PRODUCING METHOD THEREOF

(75) Inventors: Tsuyoshi Takehana, Kanagawa (JP); Ken-ichiro Nakamoto, Kanagawa (JP); Chika Itoh, Kanagawa (JP)

(73) Assignee: NOF Corporation, Tokyo (JP)

( * ) Notice: Subject to any disclaimer, the term of this patent is extended or adjusted under 35 U.S.C. 154(b) by 552 days.

(21) Appl. No.: 12/750,844

(22) Filed: Mar. 31, 2010

(65) Prior Publication Data
US 2010/0261863 A1 Oct. 14, 2010

(30) Foreign Application Priority Data

Mar. 31, 2009 (JP) ................. P2009-088461

(51) Int. Cl.
*C08G 65/34* (2006.01)

(52) U.S. Cl.
USPC ........................................... 528/425

(58) Field of Classification Search
None
See application file for complete search history.

(56) References Cited

U.S. PATENT DOCUMENTS

| | | | |
|---|---|---|---|
| 5,371,251 A * | 12/1994 | Hamann et al. | 554/97 |
| 8,329,191 B2 * | 12/2012 | Jo et al. | 424/198.1 |
| 2003/0065134 A1 | 4/2003 | Sakanoue et al. | |
| 2005/0058620 A1 | 3/2005 | Nakamoto | |
| 2005/0288490 A1 * | 12/2005 | Nakamoto et al. | 530/385 |
| 2008/0081888 A1 | 4/2008 | Kubo et al. | |
| 2010/0029899 A1 | 2/2010 | Sakanoue | |
| 2010/0113731 A1 | 5/2010 | Hayashi et al. | |

FOREIGN PATENT DOCUMENTS

| | | |
|---|---|---|
| GB | 1 453 385 | 10/1976 |
| JP | 50-089405 A | 7/1975 |
| JP | 62-127378 A | 6/1987 |
| JP | 2-242823 A | 9/1990 |
| JP | 06-087819 A | 3/1994 |
| JP | 2000-001541 A | 1/2000 |
| JP | 2000001542 A | 1/2000 |
| JP | 2000044674 A | 2/2000 |
| JP | 2003-113241 A | 4/2003 |
| JP | 2004-197077 A | 7/2004 |
| JP | 2008-106269 A | 5/2008 |
| JP | 2008248232 A | 10/2008 |
| JP | 2008-274241 A | 11/2008 |
| JP | 2009-280652 A | 12/2009 |
| WO | WO 2008060002 A1 * | 5/2008 |

* cited by examiner

*Primary Examiner* — Ling Choi
*Assistant Examiner* — Catherine S Branch
(74) *Attorney, Agent, or Firm* — Sughrue Mion, PLLC

(57) ABSTRACT

A multibranched polyoxyalkylene compound represented by the following formula (1):

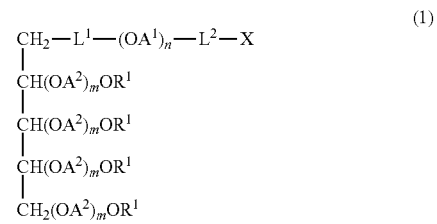

wherein $R^1$ is the same or different and is a hydrocarbon group having 1 to 24 carbon atoms, $OA^1$ and $OA^2$ are the same or different and are an oxyalkylene group having 2 to 4 carbon atoms, n and m are the same or different and are an average number of moles of the oxyalkylene group added, n represents 0 to 1000, m is the same or different and represents 10 to 1000, X represents a functional group capable of reacting with an amino group, a mercapto group, an aldehyde group, a carboxyl group, a triple bond, or an azide group to form a chemical bond, and $L^1$ and $L^2$ are the same or different and are a single bond, an alkylene group, or an alkylene group in which at least one bond selected from an ester bond, a urethane bond, an amide bond, an ether bond, and an amino is interposed.

14 Claims, No Drawings

MULTIBRANCHED POLYOXYALKYLENE COMPOUND AND PRODUCING METHOD THEREOF

TECHNICAL FIELD

The present invention relates to a multibranched polyoxyalkylene compound to be used in applications for modifying bio-related substances, and a method for obtaining a production intermediate for the multibranched polyoxyalkylene compound.

BACKGROUND ART

With the advance in genetic engineering, recently, development and studies on medicaments have been actively carried out, which use bio-related substances such as intercellular signaling substances such as hormones and cytokines, antibodies, and enzymes. Since these bio-related substances are usually cleared from a living body because of the filtration through glomeruli in the kidney and the uptake by macrophages in the liver, spleen, and the like when the substances are injected to the body, they have short half-lives in blood and hence it is difficult to obtain a sufficient pharmacological effect. For solving the problems, it is attempted to improve the behavior in a living body by including the bio-related substances in liposomes or polymer micelles or increasing their molecular weight or forming a hydration layer through chemical modification with an amphiphatic polymer such as a sugar chain or polyethylene glycol or albumin. In the modification with a polyoxyalkylene compound, effects of decreasing toxicity and antigenicity and enhancing solubility of sparingly water-soluble pharmaceuticals are also obtained but, excessive modification of the polyoxyalkylene compound breaks the active points of the bio-related substances and reduces functions thereof, so that it is attempted to enhance the effects by increasing the molecular weight of the polyoxyalkylene compound. However, since an increase in the molecular weight results in an increase in viscosity in the polyoxyalkylene compound, there arises a problem that it is difficult to handle it, for example, in solution preparations such as an injection preparation, so that there has been advanced the development of polyoxyalkylene compounds having a branched structure in which viscosity is improved.

Patent Document 1 describes a polyoxyalkylene compound which branches into two chains. This is a compound in which two polyoxyalkylene chains form, together with glycerin, an ether bond which is hardly decomposed into one chain.

Furthermore, as a polyoxyalkylene compound having a multibranched structure, Patent Documents 2 and 3 describe a polyoxyalkylene compound having a tetrabranched structure containing triglycerin as a fundamental skeleton. However, since it uses triglyceryl monoallyl ether as a starting material, in the case where the allyl ether part is subjected to functional group conversion, the conversion is limited to compounds having a sulfur atom. Moreover, in the case where polymerization reaction with an alkylene oxide is carried out under an alkali catalyst, there is a concern that the allyl ether is rearranged into a propenyl ether and then converted into a hydroxyl group during a neutralization step, resulting in a decrease in purity.

Patent Document 4 describes a polyoxyalkylene compound having a tetrabranched structure containing 1,2-glycerol as a fundamental skeleton. This is a polyoxyalkylene compound having a dibranched plus tetrabranched structure in which polyoxyalkylene terminal ends having a dibranched structure further branch into dibranched chains. However, since the compound has the dibranched structure in the molecule, in the case where it is transformed into an aqueous solution, it is considered that the compound shows a high viscosity as compared with a polyoxyalkylene compound having only a tetrabranched chain. Moreover, also in synthesis, since the structure is complex, there is a problem that a variety of impurities form.

As described above, a polyoxyalkylene compound having a multibranched group chain structure of four or more chains capable of being effectively used in applications for modifying bio-related substances and industrially easily produced is not obtained, so that it has been desired an appearance of such a multibranched polyoxyalkylene compound.

BACKGROUND ART REFERENCES

Patent Documents

[Patent Document 1] JP-A-2004-197077
[Patent Document 2] JP-A-2000-1542
[Patent Document 3] JP-A-2000-44674
[Patent Document 4] JP-A-2008-248232

SUMMARY OF THE INVENTION

Problems that the Invention is to Solve

An object of the present invention is to provide a multibranched polyoxyalkylene compound exhibiting a low viscosity in an aqueous solution and having four chains formed with an ether bond as well as a producing method thereof.

Means for Solving the Problems

As a result of the extensive studies for solving the above problems, the present inventors have found out a multibranched polyoxyalkylene compound and a producing method thereof, and thus they have accomplished the invention.

Namely, the invention relates to:

[1] A multibranched polyoxyalkylene compound represented by the following formula (1):

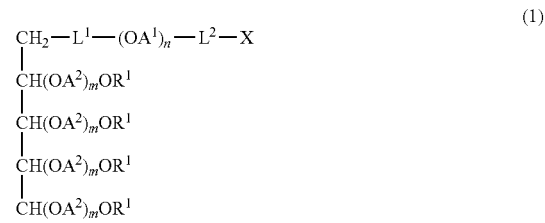

wherein $R^1$ is the same or different and is a hydrocarbon group having 1 to 24 carbon atoms, $OA^1$ and $OA^2$ are the same or different and are an oxyalkylene group having 2 to 4 carbon atoms, n and m are the same or different and are an average number of moles of the oxyalkylene group added, n represents 0 to 1000, m is the same or different and represents 10 to 1000, X represents a functional group capable of reacting with an amino group, a mercapto group, an aldehyde group, a carboxyl group, a triple bond, or an azide group to form a chemical bond, and $L^1$ and $L^2$ are the same or different and are a single bond, an alkylene group, or an alkylene group in which at least one bond selected from an ester bond, a urethane bond, an amide bond, an ether bond, a carbonate bond, and an amino is interposed.

[2] The multibranched polyoxyalkylene compound according to [1], wherein $R^1$ is the same or different and is a hydrocarbon group having 1 to 10 carbon atoms and $OA^1$ and $OA^2$ are the same or different and are an oxyalkylene group having 2 to 3 carbon atoms in the above formula (1).

[3] The multibranched polyoxyalkylene compound according to [1], wherein $R^1$ is a methyl group and $OA^1$ and $OA^2$ are an oxyethylene group in the above formula (1).

[4] The multibranched polyoxyalkylene compound according to [1], wherein m is the same or different and is 50 to 1000 in the above formula (1).

[5] The multibranched polyoxyalkylene compound according to [1], wherein m is the same or different and is 100 to 800 in the above formula (1).

[6] The multibranched polyoxyalkylene compound according to [1], wherein n is 0 in the above formula (1).

[7] The multibranched polyoxyalkylene compound according to [1], wherein n is 1 to 1000 in the above formula (1).

[8] The multibranched polyoxyalkylene compound according to [1], wherein n is 200 to 1000 in the above formula (1).

[9] The multibranched polyoxyalkylene compound according to [1], wherein X is a functional group selected from the group consisting of an activated ester, a carbonate, an aldehyde, a thiol, a maleimide that may be substituted, a dithiopyridine, a sulfone, an amine, an oxyamine, a hydrazide, an α-haloacetyl, a carboxylic acid, a triple bond, and an azide in the above formula (1).

[10] The multibranched polyoxyalkylene compound according to [1], wherein, in the above formula (1), X is a functional group selected from the group consisting of:

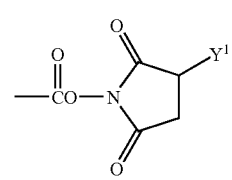
(a)

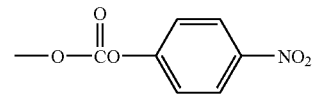
(b)

—CHO (c)

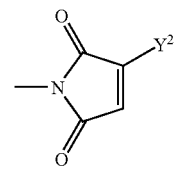
(d)

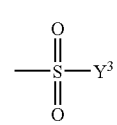
(e)

—COOH (f)

—SH (g)

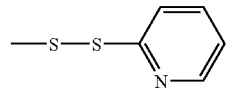
(h)

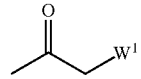
(i)

—C≡CH (j)

—NH$_2$ (k)

—O—NH$_2$ (l)

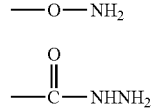
(m)

—N$_3$ (n)

where $Y^1$ is a hydrogen atom or a sulfonyl group, $Y^2$ is a hydrogen atom or a hydrocarbon group having 1 to 3 carbon atoms, $Y^3$ is a hydrocarbon group having 1 to 10 carbon atoms that may contain a fluorine atom or an alkoxy having 1 to 3 carbon atoms that may be substituted with a fluorine atom, and $W^1$ is a halogen atom.

[11] A multibranched polyoxyalkylene compound represented by the following formula (2):

$$\begin{array}{l} CH_2-L^1-(OA^1)_n-OH \\ CH(OA^2)_mOR^1 \\ CH(OA^2)_mOR^1 \\ CH(OA^2)_mOR^1 \\ CH(OA^2)_mOR^1 \end{array} \quad (2)$$

wherein $R^1$ is the same or different and is a hydrocarbon group having 1 to 24 carbon atoms, $OA^1$ and $OA^2$ are the same or different and are an oxyalkylene group having 2 to 4 carbon atoms, n and m are the same or different and are an average number of moles of the oxyalkylene group added, n represents 0 to 1000, m is the same or different and represents 10 to 1000, and $L^1$ represents a single bond, an alkylene group, or an alkylene group in which at least one bond selected from an ester bond, a urethane bond, an amide bond, an ether bond, a carbonate bond, and an amino is interposed.

[12] A producing method of the multibranched polyoxyalkylene compound according to [1], which comprises the following steps (A2) to (A4):

Step (A2): a step of reacting a compound represented by the following formula (3):

$$\begin{array}{l} CH_2-OR^2 \\ CHOH \\ CHOH \\ CHOH \\ CH_2OH \end{array} \quad (3)$$

wherein $R^2$ is a hydrocarbon group having 1 to 24 carbon atoms, with an alkylene oxide to obtain a compound represented by the following formula (4):

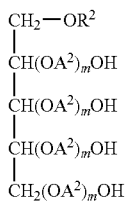
(4)

wherein $R^2$ is a hydrocarbon group having 1 to 24 carbon atoms, $OA^2$ is the same or different and is an oxyalkylene group having 2 to 4 carbon atoms, m is the same or different and is an average number of moles of the oxyalkylene group added, and m is the same or different and represents 10 to 1000, Step (A3): on the compound represented by the above formula (4), a step of etherifying the terminal hydroxyl group of the multibranched polyoxyalkylene and, after deprotection of $R^2$, introducing a group containing $L^1$ in the case where $L^1$ is not a single bond or an oxyalkylene in the case where n is 1 or more, thereby obtaining a compound represented by the following formula (2):

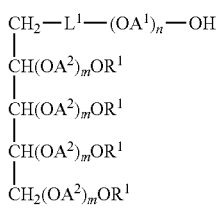
(2)

wherein $R^1$ is the same or different and is a hydrocarbon group having 1 to 24 carbon atoms, $OA^1$ and $OA^2$ is the same or different and is an oxyalkylene group having 2 to 4 carbon atoms, n and m is the same or different and is an average number of moles of the oxyalkylene group added, n represents 0 to 1000, m is the same or different and represent 10 to 1000, and $L^1$ represents a single bond, an alkylene group, or an alkylene group in which at least one bond selected from an ester bond, a urethane bond, an amide bond, an ether bond, a carbonate bond, and an amino is interposed, and Step (A4): a step of converting the hydroxyl group of the compound represented by the above formula (2) into -$L^2$-X where $L^2$ is the same or different and represents a single bond, an alkylene group, or an alkylene group in which at least one bond selected from an ester bond, a urethane bond, an amide bond, an ether bond, a carbonate bond, and an amino is interposed and X represents a functional group capable of reacting with an amino group, a mercapto group, an aldehyde group, a carboxyl group, a triple bond, or an azide group to form a chemical bond.

[13] The producing method of the multibranched polyoxyalkylene compound, according to claim 12, wherein, as a compound represented by the following formula (3):

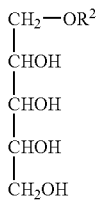
(3)

wherein $R^2$ is a hydrocarbon group having 1 to 24 carbon atoms, the compound obtained by the following step (B1) is used:

Step (B1): a step of protecting the hydroxyl group of a compound represented by the following formula (6):

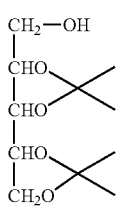
(6)

to obtain a compound represented by the following formula (5):

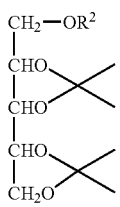
(5)

wherein $R^2$ is the same as above, and subsequently obtaining the compound represented by the following formula (3):

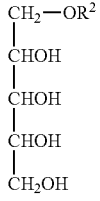
(3)

wherein $R^2$ is the same as above,
by acid hydrolysis.

[14] The producing method of the multibranched polyoxyalkylene compound, according to claim 13, wherein, as a compound represented by the following formula (6):

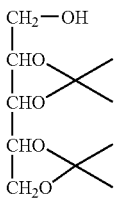
(6)

the compound obtained by the following steps (C1) and (C2) is used:

Step (C1): a step of ketalizing xylitol to obtain a mixture of compounds represented by the following formula (6) and the following formula (7):

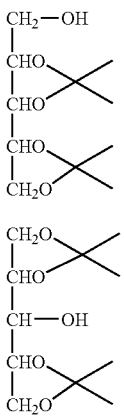

subsequently reacting the mixture with a silicon compound represented by the following formula (8):

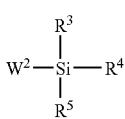
(8)

wherein $W^2$ is a halogen atom or an alkylsulfonate having 1 to 3 carbon atoms that may be substituted with 1 to 3 halogen atoms and $R^3$, $R^4$, and $R^5$ are a hydrocarbon group having 1 to 10 carbon atoms and are the same or different from one another in the same molecule, and a tertiary amine to obtain a mixture of compounds represented by the following formula (9):

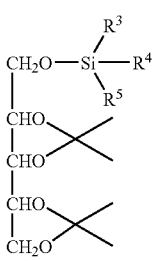
(9)

wherein $R^3$, $R^4$, and $R^5$ represent groups the same as above, and the compound represented by the above formula (7), and subsequently separating the compound represented by the above formula (9) from the mixture, Step (C2): a step of reacting the compound represented by the above formula (9) with a desilylation agent to obtain the compound represented by the above formula (6).

Advantage of the Invention

The novel multibranched polyoxyalkylene compound (1) (multibranched polyoxyalkylene compound represented by the formula (1)) according to the invention improves hitherto known viscosity in the same molecular weight and, in the case where the compound is utilized to modify bio-related substances to use in pharmaceutical applications such as aqueous solution preparations such as an injection preparation, it is considered that influence of the viscosity by the polyoxyalkylene compound is improved. Moreover, according to the producing method, a variety of impurities are hardly produced and a multibranched polyoxyalkylene compound having four chains formed with an ether bond can be produced in good purity. Since the hydroxyl group at the 1-position of xylitol in the compound is derivatized into a functional group capable of chemical bonding with a bio-related substance, it is considered that the compound can be bonded without steric reaction inhibition in the case of the reaction with the bio-related substance.

MODE FOR CARRYING OUT THE INVENTION

In the present specification, a "halogen atom" or "halo" means a fluorine atom (F), a chlorine atom (Cl), a bromine atom (Br), or an iodine atom (I) unless otherwise stated.

$R^1$ in the polyoxyalkylene group in the formula (1) of the invention is a hydrocarbon group having 1 to 24 carbon atoms, and the hydrocarbon group having 1 to 24 carbon atoms includes a linear or branched alkyl group having 1 to 24 carbon atoms, an aryl group having 6 to 24 carbon atoms, and a linear or branched arylalkyl group having 7 to 24 carbon atoms. The hydrocarbon groups represented by a plurality of $R^1$'s in the formula (1) may be the same or different.

Specific groups in $R^1$ include hydrocarbon groups such as a methyl group, an ethyl group, a propyl group, an isopropyl group, a butyl group, a tert-butyl group, a pentyl group, an isopentyl group, a hexyl group, a heptyl group, a 2-ethylhexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, an oleyl group, a nonadecyl group, an eicosyl group, a heneicosyl group, a docosyl group, a tricosyl group, a tetracosyl group, a benzyl group, a butylphenyl group, and a dodecylphenyl group. Preferred are cases of hydrocarbon groups having 1 to 10 carbon atoms, more preferred are cases of a methyl group and an ethyl group, and further preferred is a case of a methyl group.

$OA^1$ and $OA^2$ are the same or different and represent an oxyalkylene group having 2 to 4 carbon atoms. Specifically, there may be mentioned an oxyethyl group, an oxypropyl group, an oxytrimethylene group, an oxy-1-ethylethylene group, an oxy-1,2-dimethylethylene group, an oxytetramethylene group, and the like. The oxyalkylene groups represented by $OA^1$ and $OA^2$ may be the same or different and the oxyalkylene groups in respective symbols are the same or different in the same symbol. Namely, the polymer of the invention may be one randomly added or one added in a block form as an addition manner in each branch. In general, an alkyl group having smaller number of carbon atoms has higher hydrophilicity, and preferred are an oxyethylene group and an oxypropylene group and more preferred is an oxyethylene group.

m and n are the same or different and are an average number of moles of the oxyalkylene group added. m is the same or different and is 10 to 1000, preferably 50 to 1000, and further preferably 100 to 800. n is 0 to 1000, and there is a case where the case that n is 0 is preferred or a case where the case that n is 1 or more is preferred depending on use purposes. In the case where it is intended to reduce steric hindrance by the polyoxyalkylene group in the functional group capable of bonding to a bio-related substance, there may be mentioned a method of introducing an oxyalkylene group between the xylitol residue and the functional group. Preferred is the case that n is 1 or more and the upper limit is preferably 1000 or less. n is more preferably 20 to 1000, further preferably 50 to 1000, and most preferably 200 to 1000. A plurality of m's in the formula (1) may be the same or different.

m and n can be determined by measuring an average molecular weight on the synthesized branched polyoxyalkylene compound or a synthetic intermediate thereof and converting the average molecular weight. The average molecular weight in this case is a molecular weight measured by the TOF-MASS method, and the measuring method and conditions and the like are as described below.

In the TOF-MS analysis, Bruker autoflex III is used.

The preparation of the measuring sample is carried out as follows.

A sample is dissolved in a THF solution prepared from 1,8,9-anthracenetriol and sodium trifluoroacetate to prepare a measuring sample.

An average number of moles of the oxyalkylene group added, m or n, can be controlled by calculating a necessary amount of an alkylene oxide from a numeral formula in which the molecular weight of the alkylene oxide is represented as a variable number of m and/or n and reacting the alkylene oxide in an alkylene oxide polymerization reaction (step (A2) or the like) to be mentioned below.

In the formula, X is not particularly limited as far as it is a functional group capable of reacting with an amino group, a mercapto group, an aldehyde, a carboxyl group, a triple bond, or an azide group to form a chemical bond but there may be mentioned known functional groups presented in Bioconjugate Techniques, Second Edition By Greg T. Hermanson Published by Academic Press, Inc., 2008 and the like. Specifically, they are functional groups shown by an activated ester, a carbonate, a thiol, a maleimide that may be substituted, a dithiopyridine, a sulfone, an amine, an oxyamine, a hydrazide, an α-haloacetyl, a carboxylic acid, a triple bond, an azide, and the like.

The "active ester" shows a group represented by the formula: —C(=O)-L and L represents a leaving group. The leaving group represented by L includes succinimidyloxy, phthalimidyloxy, 5-norbornen-2,3-dicarboxyimidyloxy, p-nitrophenoxy, pentafluorophenoxy, benzotriazol-1-yloxy, 6-chlorobenzotriazol-1-yloxy, 7-azabenzotriazol-1-yloxy, 3,4-dihydro-4-oxo-1,2,3-benzotriazin-3-yloxy, and the like. As a substituent of the succinimidyloxy, a sulfonyl group may be mentioned. The sulfonyl group includes sodium sulfonate, potassium sulfonate, and the like.

The "carbonate" shows a group represented by the formula: —O—C(=O)-L and L represents a leaving group the same as above.

The "sulfone" shows a group represented by the formula: —SO$_2$—Y and Y represents a hydrocarbon group having 1 to 10 carbon atoms that may be substituted. Here, the "hydrocarbon group having 1 to 10 carbon atoms" includes a methyl group, an ethyl group, a propyl group, an isopropyl group, a butyl group, a tert-butyl group, a pentyl group, an isopentyl group, a hexyl group, a heptyl group, a 2-ethylhexyl group, an octyl group, a nonyl group, a decyl group, a benzyl group, and a butylphenyl group. The substituent of the hydrocarbon group includes a halogen atom or an alkoxy group having 1 to 3 carbon atoms that may be substituted by a halogen atom (e.g., methoxy, ethoxy, or trifluoromethoxy, etc.).

The substituent of the maleimide includes an alkyl group having 1 to 3 carbon atoms (e.g., an alkyl group having 1 to 3 carbon atoms, such as methyl, ethyl, or propyl).

Further specifically, in X, the functional group capable of reacting with an amino group to form a chemical bond is an activated ester, a carbonate, an aldehyde, a maleimide, a sulfone, or a carboxylic acid; the functional group capable of reacting with a mercapto group to form a chemical bond is an activated ester, a carbonate, an aldehyde, a maleimide, a sulfone, a carboxylic acid, a thiol, a dithiopyridine, an α-haloacetyl, or a triple bond; the functional group capable of reacting with an aldehyde or a carboxyl group to form a chemical bond is a thiol, an amine, an oxyamine, or a hydrazine; the functional group capable of reacting with a triple bond to form a chemical bond is a thiol, an amine, an oxyamine, a hydrazide, or an azide; and the functional group capable of reacting with an azide group to form a chemical bond is a triple bond.

Preferred are embodiments wherein X is a functional group selected from the group consisting of:

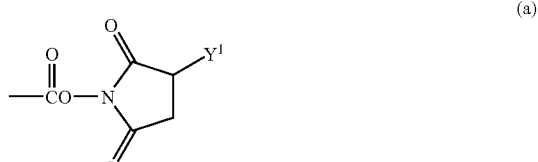

(a)

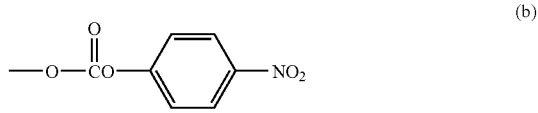

(b)

(c)

(d)

(e)

(f)

—COOH

(g)

—SH

(h)

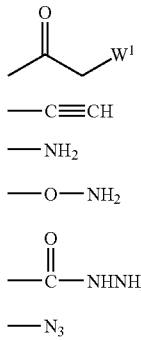

(i)

—C≡CH (j)

—NH$_2$ (k)

—O—NH$_2$ (l)

(m)

$$\overset{O}{\underset{\|}{-C}}-NHNH_2$$

—N$_3$ (n)

wherein Y$^1$ is a hydrogen atom or a sulfonyl group, Y$^2$ is a hydrogen atom or a hydrocarbon group having 1 to 3 carbon atoms, Y$^3$ is a hydrocarbon group having 1 to 10 carbon atoms that may contain a fluorine atom or an alkoxy having 1 to 3 carbon atoms that may be substituted with a fluorine atom, and W$^1$ is a halogen atom.

In this regard, Y$^1$ is a hydrogen atom or a sulfonyl group and the sulfonyl group specifically includes sodium sulfonate and potassium sulfonate, but preferred is a case of a hydrogen atom. Moreover, Y$^2$ is a hydrogen atom or a hydrocarbon group having 1 to 3 carbon atoms and the hydrocarbon group specifically includes hydrocarbon groups having 1 to 3 carbon atoms such as a methyl group, an ethyl group, and a propyl group, but preferred is a case of a hydrogen atom. Y$^3$ is a hydrocarbon group having 1 to 10 carbon atoms that may contain 1 to 3 fluorine atoms or an alkoxy having 1 to 3 carbon atoms that may be substituted with 1 to 7 fluorine atoms and the hydrocarbon group includes linear or branched alkyl groups having 1 to 10 carbon atoms, linear or branched alkenyl groups having 2 to 10 carbon atoms, linear or branched alkynyl groups having 2 to 10 carbon atoms, aryl groups having 6 to 10 carbon groups, linear or branched arylalkyl groups having 7 to 10 carbon atoms, linear or branched arylalkenyl groups having 8 to 24 carbon atoms, linear or branched arylalkynyl groups having 8 to 24 carbon atoms, and linear or branched alkylaryls having 7 to 10 carbon atoms. Specifically, there may be mentioned a methyl group, an ethyl group, a propyl group, an isopropyl group, a butyl group, a tert-butyl group, a hexyl group, a nonyl group, a vinyl group, a phenyl group, a benzyl group, a 4-methylphenyl group, a trifluoromethyl group, a 2,2,2-trifluoroethyl group, 4-(trifluoromethoxy)phenyl group, and the like but preferred are cases of a methyl group, a vinyl group, a 4-methylphenyl group, and a 2,2,2-trifluoroethyl group.

In the formula, the halogen atom represented by W$^1$ includes Cl, Br, I, and the like but preferred is a case of I.

In the "functional group capable of reacting with an amino group, a mercapto group, an aldehyde, a carboxyl group, a triple bond, or an azide group" in X, which is exemplified in the above, the "amino group, mercapto group, aldehyde, carboxyl group, triple bond, or azide group" that is a reaction target of X is a functional group capable of existing in a bio-related substance and the multibranched polyoxyalkylene compound of the invention is capable of forming a chemical bond with the bio-related substance.

In the present description, the "bio-related substance" specifically includes substances exemplified by intercellular signaling substances such as hormones and cytokines, animal cell-constituting substances such as antibodies, enzymes, phospholipids, and glycolipids, and body fluid-constituting substances such as blood and lymph but is not limited thereto and is intended to substances existing in living bodies of various organisms or substances which are converted into them in the living bodies, analogs thereof, or mimics thereof, or substances which interact with substances existing in the living bodies to express physiological activity.

In a preferred embodiment in the reaction of the compound of the invention with a bio-related substance, X is a group shown in the following Group (I), Group (II), Group (III), Group (IV), or Group (V).

Group (I): functional groups capable of reacting with an amino group of bio-related substances
aforementioned (a), (b), (c), (d), (e), (f)

Group (II): functional groups capable of reacting with a mercapto group of bio-related substances
aforementioned (a), (b), (c), (d), (e), (f), (g), (h), (i), (j)

Group (III): functional groups capable of reacting with an aldehyde or carboxyl group of bio-related substances
aforementioned (g), (k), (l), (m)

Group (IV): functional groups capable of reacting with a triple bond of bio-related substances
aforementioned (g), (k), (l), (m), (n)

Group (V): functional groups capable of reacting with an azide group of bio-related substances
aforementioned (j)

L$^1$ is a linker between a xylitol residue and a polyoxyalkylene group [(OA$^1$)n] and L$^2$ is a linker between the polyoxyalkylene group [(OA$^1$)n] and a reactive functional group [X].

There is a case where the linker is not present and, in that case, L$^1$ and L$^2$ are defined as a single bond.

L$^1$ and L$^2$ are not particularly limited as far as they are a covalent bond but preferably include an alkylene group, an alkylene group in which at least one bond selected from an ester bond (—C(=O)—O— or —O—C(=O)—), a urethane bond (—NH—C(=O)—O— or —O—C(=O)—NH—), an amide bond (—C(=O)—NH— or —NH—C(=O)—), an ether bond (—O—), a carbonate bond (—O—C(=O)—O—), and an amino (—NH—) is interposed, or the like. Here, the "alkylene group in which a bond is interposed" means that the bond is interposed between any of the carbon-carbon bonds of the alkylene chain.

The "alkylene group" in L$^1$ and L$^2$ is preferably an alkylene group having 1 to 12 carbon atoms and specifically includes a methylene group, an ethylene group, a trimethylene group, a propylene group, an isopropylene group, a tetramethylene group, a butylene group, an isobutylene group, a pentamethylene group, a hexamethylene group, and the like.

L$^1$ and L$^2$ include groups represented by the structural formula of the following (z1), the structural formula of the following (z2), the structural formula of the following (z3), the structural formula of the following (z4), the structural formula of the following (z5), and the structural formula of the following (z6).

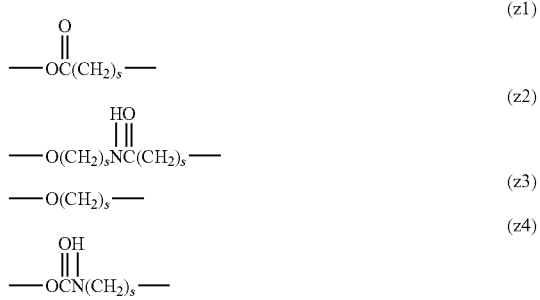

-continued

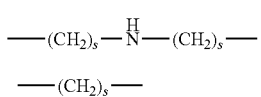
(z5)

—(CH$_2$)$_s$—

(z6)

wherein s is an integer of 0 to 6, preferably s is an integer of 0 to 3, and further preferably an integer of 1 to 3; in the case where two s's are present, they may be the same or different.

In the compound represented by the formula (2), $R^1$, $OA^1$, $OA^2$, $L^1$, m, and n are the same as mentioned above.

The multibranched polyoxyalkylene compound (2) (multibranched polyoxyalkylene compound represented by the formula (2)) of the invention can be produced as follows, for example.

Four hydroxyl groups of xylitol are subjected to cyclic ketalization to obtain an isomer mixture of 1,2,3,4-diisopropylidenexylitol represented by the formula (6) and 1,2,4,5-diisopropylidenexylitol represented by the formula (7) and the isomer mixture is reacted with a silicon compound represented by the formula (8) and a tertiary amine to protect only the primary hydroxyl group of 1,2,3,4-diisopropylidenexylitol (6) selectively, thereby obtaining a mixture of the compound represented by the formula (9) and 1,2,4,5-diisopropylidenexylitol (7) (step (C1)).

1,2,4,5-Diisopropylidenexylitol (7) remaining in the mixture is removed to isolate the compound (9) and then the compound (9) is reacted with a desilylation agent to achieve deprotection, thereby isolating 1,2,3,4-diisopropylidenexylitol (6) (step (C2)).

The primary hydroxyl group residue of the isolated 1,2,3,4-diisopropylidenexylitol (6) is protected with $R^2$ (e.g., a benzyl group, a t-Bu group) to obtain a compound represented by the formula (5), which is then hydrolyzed under an acidic condition to deprotect the cyclic ketal structure, thereby obtaining a compound represented by the formula (3) (step (B1)).

Then, the multibranched polyoxyalkylene compound represented by the formula (2) can be obtained by polymerizing an alkylene oxide in 10 to 1000 moles to newly formed four hydroxyl groups to obtain a compound represented by the formula (4) (step (A2)), subjecting the terminal to alkyl etherification, then deprotecting the protective group of $R^2$, and further introducing a group containing $L^1$ in the case where $L^1$ is not a single bond and introducing an oxyalkylene in the case where n is 1 or more (step (A3)).

In the case where n is 0 in the formula, the compound (2) where n is 0 can be obtained by carrying out the process with skipping the oxyalkylene-introducing step in the step (A3).

The following shows a reaction path for the compound (2).

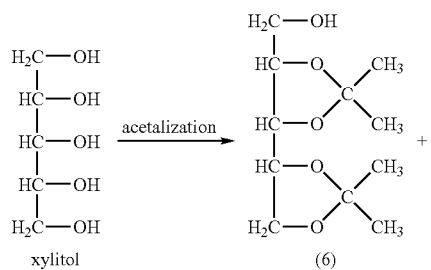

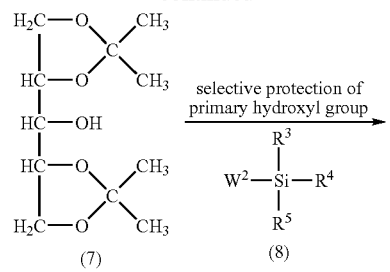

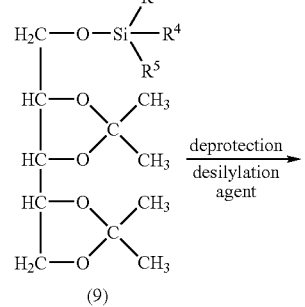

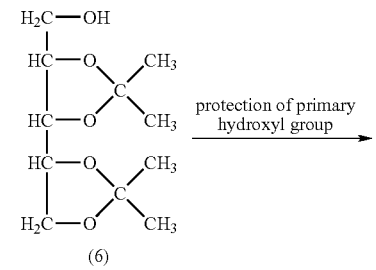

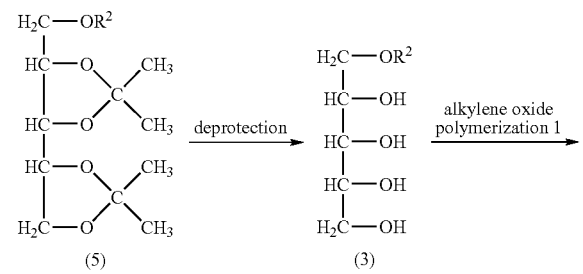

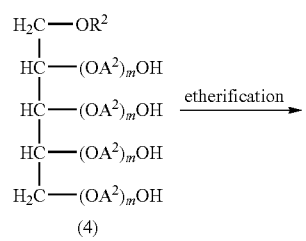

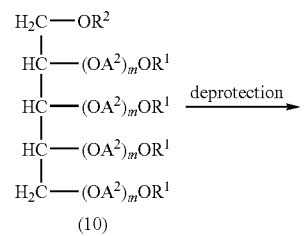

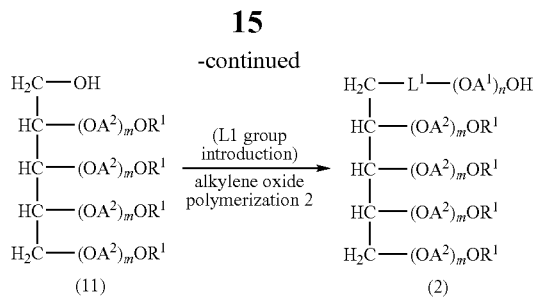

wherein respective symbols are the same as above.

Moreover, the compound (2) wherein $L^1$ is a single bond and n is 1 or more can be also produced by the following process.

An alkylene oxide is polymerized in an amount of 1 to 1000 moles to the primary hydroxyl group residue of 1,2,3,4-diisopropylidenexylitol (6) from which the structural isomer is removed to obtain a compound represented by the formula (12), the terminal hydroxyl group of the compound (12) is protected with $R^2$ (e.g., a benzyl group, a t-Bu group, or the like) to obtain a compound represented by the formula (13), which is then hydrolyzed under an acidic condition to deprotect the cyclic ketal structure, obtaining a compound represented by the formula (14). An alkylene oxide is polymerized in an amount of 10 to 1000 moles to the newly formed four hydroxyl groups of the compound (14) to obtain a compound represented by the formula (15) and the terminal hydroxyl groups of the compound (15) are subjected to alkyl etherification. Then, the multibranched polyoxyalkylene compound represented by the formula (2) can be obtained by deprotecting the protective group of $R^2$.

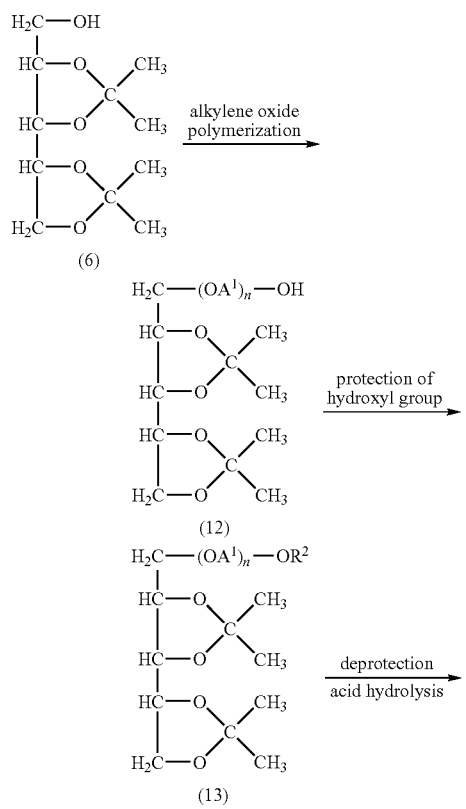

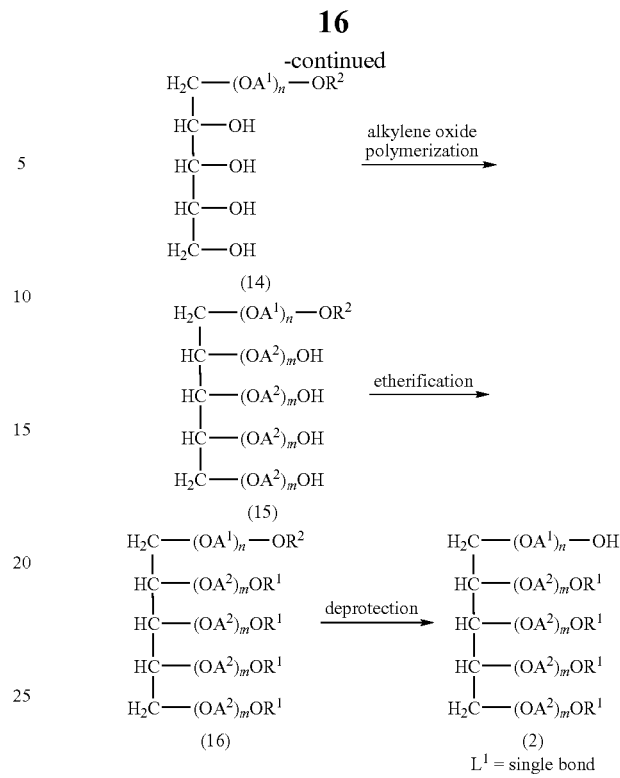

wherein respective symbols are the same as above.

Moreover, in addition to the above, for example, the compound (2) wherein $L^1$ is $-OC(=O)NH(CH_2)_2-$ and n is 1 or more can be also produced by the following process.

After the primary hydroxyl group residue of 1,2,3,4-diisopropylidenexylitol (6) from which the structural isomer is removed is converted with a p-nitrophenyl carbonate group, an N-hydroxysuccinimidyl carbonate group, or the like into a reactive functional group to obtain a compound represented by the formula (17) (in the following scheme, only a p-nitrophenyl carbonate group is shown), the compound is reacted with an aminopolyoxyalkylene compound protected with $R^2$ (e.g., a benzyl group, a t-Bu group, or the like) to obtain a compound represented by the formula (18), which is then hydrolyzed under an acidic condition to deprotect the cyclic ketal structure, obtaining a compound represented by the formula (19). An alkylene oxide is polymerized in an amount of 10 to 1000 moles to the compound (19) to obtain a compound represented by the formula (20) and the terminal hydroxyl groups of the compound (20) are subjected to alkyl etherification. Then, the multibranched polyoxyalkylene compound represented by the formula (2) wherein $L^1$ is $-OC(=O)NH(CH_2)_2-$ and n is 1 or more can be obtained by deprotecting the protective group of $R^2$.

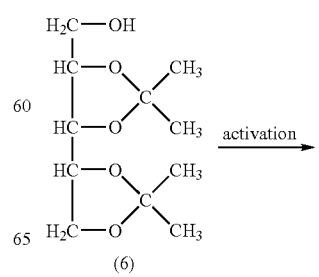

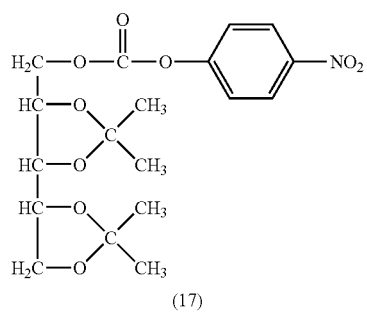

(17)

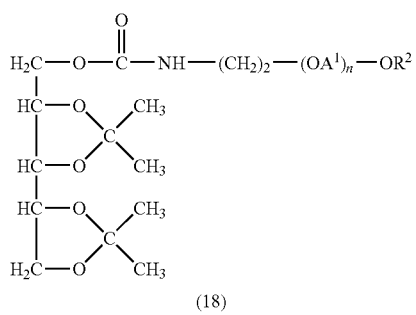

(18)

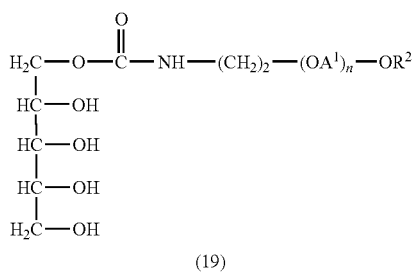

(19)

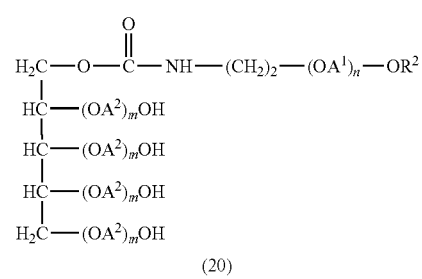

(20)

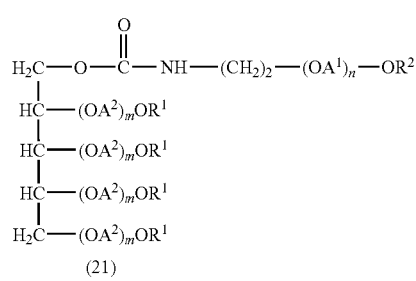

(21)

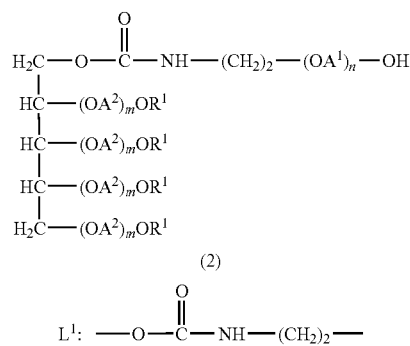

(2)

$$L^1: \quad -O-\overset{O}{\underset{\|}{C}}-NH-(CH_2)_2-$$

wherein respective symbols are the same as above.

Furthermore, the compound (2) wherein $L^1$ is —OC(=O) NH(CH$_2$)$_2$— and n is 1 or more can be also produced by the following process.

After the primary hydroxyl group residue of 1,2,3,4-diisopropylidenexylitol (6) from which the structural isomer is removed is protected with (e.g., a benzyl group, a t-Bu group, or the like) to obtain a compound represented by the formula (5), the compound (5) is hydrolyzed under an acidic condition to deprotect the cyclic ketal structure, obtaining the compound represented by the formula (3). An alkylene oxide is polymerized in an amount of 10 to 1000 moles to the compound (3) to obtain the compound represented by the formula (4) and the terminal hydroxyl group of the compound (4) is subjected to alkyl etherification. Then, the protective group of $R^2$ is deprotected to obtain a compound represented by the formula (11). After the hydroxyl group of the compound (11) is converted into a reactive functional group such as a p-nitrophenyl carbonate group or an N-hydroxysuccinimidyl carbonate group to obtain a compound represented by the formula (22) (in the following scheme, only a p-nitrophenyl carbonate group is shown), the compound (22) is reacted with an aminopolyoxyalkylene compound whose one terminal hydroxyl group is not protected or an aminopolyoxyalkylene compound whose one terminal hydroxyl group is protected with $R^2$ (e.g., a benzyl group, a t-Bu group, or the like), and then the protective group of $R^2$ is deprotected, whereby the multibranched polyoxyalkylene compound represented by the formula (2) wherein $L^1$ is —OC(=O)NH(CH$_2$)$_2$— and n is 1 or more can be obtained.

(6)

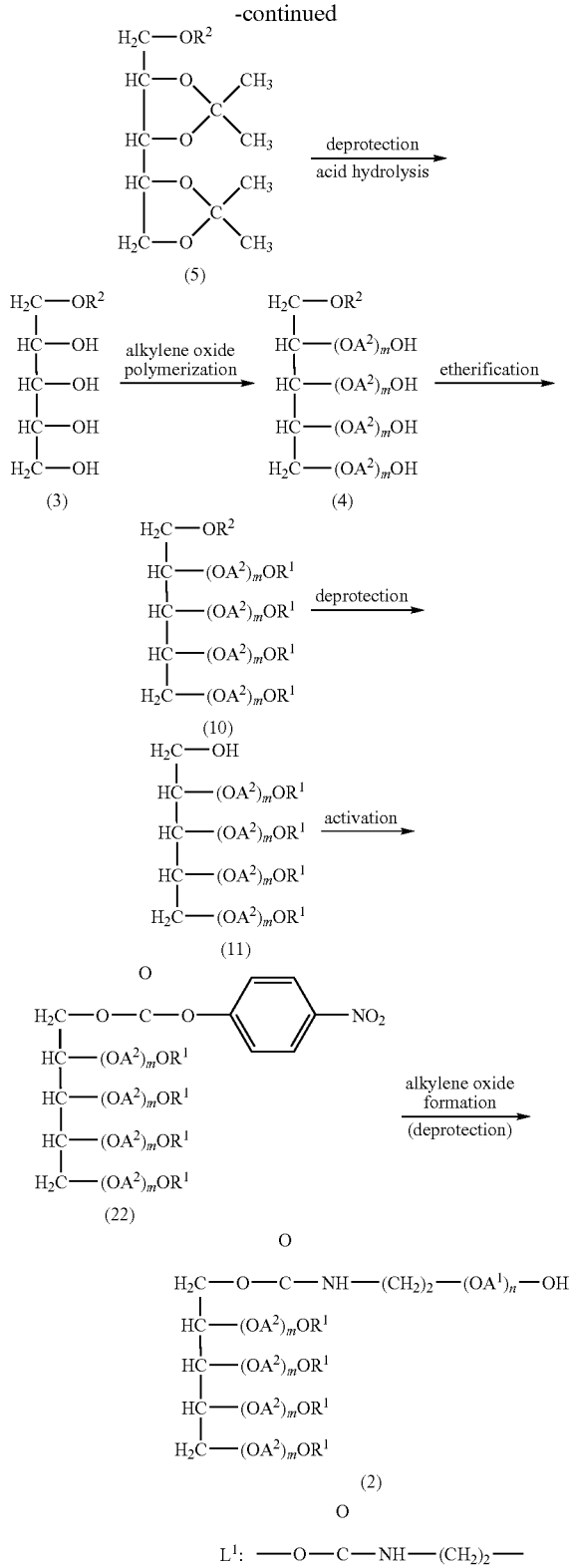

wherein respective symbols are the same as above.

As above, the multibranched polyoxyalkylene compound (2) having a high purity can be produced by industrially suitable processes in high yields without column purification by the use of alkylene oxide addition polymerization reaction using xylitol as a starting material.

The multibranched reactive polyoxyalkylene compound (1) of the invention can be produced by converting the hydroxyl group of the thus obtained compound (2) into a group represented by -$L^2$-X having one of the above various reactive groups using various chemical conversion methods.

Moreover, compounds having respective functional groups of the above Group (I), Group (II), Group (III), Group (IV), and Group (V) can be reacted with bio-related substances but, depending on cases, these compounds can be further reacted with other compounds to produce other compounds, and the other compounds can be reacted with bio-related compounds. For example, an intermediate of (a), (d), or (i) of Group (I) can be synthesized using a compound having a functional group of (f) belonging to Group (II) or (k) belonging to Group (III) as a starting material.

<Production of Intermediates>

A producing method of the compound represented by the formula (6) containing no structural isomer (7) from xylitol is not particularly limited but, for example, the compound (6) can be obtained by carrying out steps (C1) and (C2).

Step (C1): a step of obtaining a mixture of the compound represented by the formula (9) and the compound represented by the formula (7) by ketalizing xylitol to obtain a mixture of the compounds represented by the formulae (6) and (7) and then reacting the mixture with a silicon compound represented by the formula (8) and a tertiary amine to achieve silyl etherification of only the primary hydroxyl group of the compound (6) and subsequently separating the compound represented by the formula (9) from the mixture. On this occasion, molar ratios of respective charged compounds satisfy the following formulae.

Vc≧Va, and Vc>Vb

Va: sum of numbers of moles the compounds represented by the formulae (6) and (7)
Vb: number of moles of the silicon compound represented by the formula (8)
Vc: number of moles of the tertiary amine Step (C2): a step of reacting the compound represented by the formula (9) with a desilylation agent to obtain the compound represented by the formula (6). On this occasion, molar ratios of respective charged compounds satisfy the following formulae.

Vf≧Ve

Ve: number of moles of the compound represented by the formula (9)
Vf: number of moles of the desilylation agent
(Ketalization)

As methods for ketalization, there may be used methods presented in PROTECTIVE GROUPS IN ORGANIC SYNTHESIS, Fourth Edition By Peter G. M. Wuts, published by John Wiley & Sons, Inc., and the like. Specifically, a mixture of the compounds represented by the formulae (6) and (7) is obtained in a molar ratio of about 7:3 by reacting xylitol with 2,2-dimethoxypropane in the presence of an acid catalyst such as acetic acid, hydrochloric acid, phosphoric acid, p-toluenesulfonic acid, or p-toluenesulfonic acid monohydrate.

The amount of the acid to be used is preferably $5\times10^{-6}$ to $5\times10^{-4}$ equivalent, more preferably $7\times10^{-6}$ to $4\times10^{-4}$ equivalent to xylitol.

The amount of 2,2-dimethoxypropane to be used is preferably 2.4 to 3.0 equivalents, more preferably 2.6 to 3.0 equivalents to xylitol.

The reaction can be carried out in a solvent or with no solvent. In the case where a solvent is used, for example, dimethylformamide, methylene chloride, and the like can be used but no solvent is preferred.

The reaction temperature is usually 0 to 90° C., preferably 30 to 80° C. The reaction time is 1 to 24 hours.

An unketalized impurity produced in the reaction as a by-product is preferably subjected to purification. Since the hydroxyl group is protected with $R^2$ in the following or later step, $R^2$ is deprotected after polymerization with an alkylene oxide, and then a functional group is introduced, the impurity becomes an impurity capable of reacting with a bio-related substance and hence causes a decrease in purity of the objective compound. The purification is not particularly limited but column chromatography, distillation, supercritical extraction, and the like can be carried out. Suitably, purification can be achieved by distillation.

(Silyl Etherification)

The mixture of the compounds represented by the formulae (6) and (7) is reacted with the silicon compound represented by the formula (8) and a tertiary amine to convert only the primary hydroxyl group of the compound (6) into a silyl ether to obtain a mixture of compounds represented by the formulae (9) and (7) and then the compound represented by the formula (9) is separated from the mixture.

Since stirring efficiency decreases with no solvent owing to a high viscosity and the silyl etherification decreases, the reaction for the silyl etherification is preferably carried out in a reaction solvent. Solvent species is not particularly limited but there may be mentioned aprotic solvents such as tetrahydrofuran, dimethyl ether, methylene chloride, chloroform, dimethylformamide, toluene, and benzene. More preferred is methylene chloride that easily dissolves 1,2,3,4-diisopropylidenexylitol represented by the formula (6) and 1,2,4,5-diisopropylidenexylitol represented by the formula (7).

In the silicon compound represented by the formula (8), the halogen atom represented by $W^2$ includes Cl, Br, and I, and preferred is Cl. As the halogen atom represented by $W^2$ of the alkyl sulfonate having 1 to 3 carbon atoms that may be substituted with 1 to 3 halogen atoms, F, Cl, Br, and I may be mentioned, and preferred are F and Cl and more preferred is F. Moreover, the alkyl of the alkyl sulfonate having 1 to 3 carbon atoms includes methyl, ethyl, propyl, and isopropyl, and preferred are methyl and ethyl and more preferred is methyl. As specific examples of the alkyl sulfonate having 1 to 3 carbon atoms that may be substituted with 1 to 3 halogen atoms, represented by $W^2$, methanesulfonate and trifluoromethanesulfonate may be mentioned. $R^3$, $R^4$, and $R^5$ are the same or different and are a hydrocarbon group having 1 to 10 carbon atoms, and they may be the same or different from each other in the same molecule. As the above silicon compound (8), preferred is a chlorinated silane compound.

The hydrocarbon group includes linear or branched alkyl groups having 1 to 10 carbon atoms, linear or branched alkenyl groups having 2 to 10 carbon atoms, linear or branched alkynyl groups having 2 to 10 carbon atoms, aryl groups having 6 to 10 carbon groups, linear or branched arylalkyl groups having 7 to 10 carbon atoms, linear or branched arylalkenyl groups having 8 to 10 carbon atoms, linear or branched arylalkynyl groups having 8 to 10 carbon atoms, linear or branched alkylaryl groups having 7 to 10 carbon atoms, and the like.

The silicon compound (8) specifically includes chlorinated silane compounds such as chlorinated trimethylsilane, chlorinated triethylsilane, chlorinated triisopropylsilane, chlorinated dimethylisopropylsilane, chlorinated dimethylethylsilane, chlorinated tert-butyldimethylsilane, chlorinated tert-butyldiphenylsilane, and chlorinated triphenylsilane. More preferred are chlorinated tert-butyldimethylsilane, chlorinated tert-butyldiphenylsilane, chlorinated triphenylsilane, and the like, and further preferred is chlorinated tert-butyldiphenylsilane. Furthermore, the above silicon compound (8) specifically includes trimethylsilyl triflate, triethylsilyl triflate, triisopropylsilyl triflate, dimethylisopropylsilyl triflate, dimethylethylsilyl triflate, tert-butyldimethylsilyl triflate, tert-butyldiphenylsilyl triflate, triphenylsilyl triflate, trimethylsilyl mesylate, triethylsilyl mesylate, triisopropylsilyl mesylate, dimethylisopropylsilyl mesylate, dimethylethylsilyl mesylate, tert-butyldimethylsilyl mesylate, tert-butyldimethylsilyl mesylate, tert-butyldiphenylsilyl mesylate, triphenylsilyl mesylate, and the like. More preferred are tert-butyldimethylsilyl triflate, tert-butyldiphenylsilyl triflate, triphenylsilyl triflate, and the like, and further preferred is tert-butyldiphenylsilyl triflate.

The tertiary amine includes dimethylaminopyridine (DMAP), 1,8-diazabicyclo[5.4.0]undec-7-ene (DBU), 1,1,3,3-tetramethylguanidine, 1,5-diazabicyclo[4.3.0]non-5-ene (DABCO), ethyldiisopropylamine, 2,6-lutidine, and the like. They are used preferably singly or as a mixture with triethylamine or pyridine. More preferably, DMAP or DBU is used singly or as a mixture with triethylamine and, further preferably, DMAP is mixed with triethylamine. The ratio of DMAP in the mixed base is preferably 5 to less than 100% by mol, more preferably 5 to 80% by mol, and further preferably 5 to 50% by mol.

The amount Vc of the tertiary amine to be used is preferably defined by the above-defined range. When Vc is smaller than Va, the reaction does not completely proceed and the compound represented by the formula (6) remains. Moreover, when Vc is equal to or smaller than Vb, the acid produced as a by-product with the progress of the reaction cannot be trapped in good efficiency, so that the reaction ratio decreases and the compound represented by the formula (6) remains. When the compound represented by the formula (6) remains, impurities increase and the yield decreases.

The reaction temperature is usually −20 to 80° C., preferably −10 to 60° C. The reaction temperature is preferably 30 minutes to 24 hours.

In the mixture after completion of the reaction, the unreacted compound represented by the formula (7) remains. In the case where the compound represented by the formula (7) is not removed, a functional group is introduced in the following or later step and the compound is converted into an impurity having the same molecular weight as that of the objective compound. When the impurity is present, in the case where it is bonded to a bio-related substance, it becomes an impurity of the bio-related substance, which causes a decrease in purity. Therefore, it is preferred to separate the compound represented by the formula (7) in this stage by removal and purification. The purifying method is not particularly limited but the unreacted compound represented by the formula (7) is preferably removed by a purification means such as column chromatography, distillation, supercritical extraction, or the like and it is further preferred to conduct purification by distillation.

In the case of purification by distillation, it is preferred to remove the compound represented by the formula (7) at 80 to 160° C. under a vacuum degree of 10 Torr or less. In the case of 160° C. or higher, there is a concern that heat hysteresis increases to form an impurity where a ketal group is eliminated.

(Desilylation)

The compound represented by the formula (6) can be obtained from the compound represented by the formula (9) by the desilylation reaction of the step (C2) with a desilylation agent without particular limitation.

The reaction solvent is not particularly limited as far as it is aprotic solvent. The aprotic solvent includes tetrahydrofuran, dimethyl ether, methylene chloride, chloroform, dimethylformamide, toluene, and benzene, and more preferred is tetrahydrofuran. With no solvent, the viscosity of the compound represented by the formula (9) is high, the stirring efficiency decreases, and the desilylation decreases, so that there is a concern that the compound represented by the formula (9) remains.

As the desilylation agent, anhydrous one of tetrabutylammonium fluoride is preferably used but a mixed solvent of commercially available tetrabutylammonium fluoride/tetrahydrofuran may be utilized. In the case of hydrated one of tetrabutylammonium fluoride, catalytic action of tetrabutylammonium fluoride is inhibited and there is a concern that the desilylation does not proceed and the compound represented by the formula (9) remains. Moreover, an acid catalyst such as hydrochloric acid or acetic acid is not preferred since deketalization occurs together with the desilylation. With regard to the compound represented by the formula (9) and deketalized impurities, a functional group is introduced thereinto in the following or later step as in the case of the objective compound, and in the case where they are bonded to a bio-related substance, they become impurities of the desired substance and cause a decrease in purity.

The amount Vf of the desilylation agent to be used is preferably defined to the above-defined range. When Vf is smaller than Ve, the reaction does not completely proceed and the compound represented by the formula (9) remains.

The reaction temperature is preferably 60° C. or lower for suppressing side reaction, and is preferably −20° C. or higher for suppressing an increase in viscosity of the reaction liquid. The reaction time is preferably 30 minutes to 24 hours. When the time is shorter than 30 minutes, there is a concern that the reaction ratio is low. When the time is longer than 24 hours, there is a concern than a side reaction occurs.

After completion of the reaction, the purifying method of the compound represented by the formula (6) is not particularly limited but it is preferred to conduct column chromatography, distillation, extraction, supercritical extraction, or the like, and further preferred is extraction. When tetrabutylammonium fluoride as the desilylation agent and tetrabutylammonium salts contained in the formula (6) remain, they inhibit a catalyst to be used in the following step and lead to a decrease in the reaction ratio, so that it is necessary to remove them.

Although not particularly limited, the compound represented by the formula (3) can be obtained by carrying out the following step (B1) and preferably step (B2).

Step (B1): a step of protecting the hydroxyl group of the compound represented by the formula (6) to obtain the compound represented by the formula (5) and subsequently obtaining the compound represented by the formula (3) by acid hydrolysis.

Step (B2): a step of repeatedly washing the aqueous solution obtained in the step (B1) with a water-insoluble organic solvent.

(Protection of Hydroxyl Group)

$R^2$ as a protective group is a hydrocarbon group having 1 to 24 carbon atoms and, the hydrocarbon group having 1 to 24 carbon atoms includes linear or branched alkyl groups having 1 to 24 carbon atoms, aryl groups having 6 to 24 carbon atoms, and linear or branched arylalkyl groups having 7 to 24 carbon atoms.

Specific groups in the above $R^2$ include hydrocarbon groups such as a methyl group, an ethyl group, a propyl group, an isopropyl group, a butyl group, a tert-butyl group, a pentyl group, an isopentyl group, a hexyl group, a heptyl group, a 2-ethylhexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, an oleyl group, a nonadecyl group, an eicosyl group, a heneicosyl group, a docosyl group, a tricosyl group, a tetracosyl group, a benzyl group, a butylphenyl group, and a dodecylphenyl group. Preferred are cases of hydrocarbon groups having 1 to 10 carbon atoms, more preferred are cases of a tert-butyl group and a benzyl group, and further preferred is a case of a benzyl group.

In the present protecting step, for example, known methods presented in PROTECTIVE GROUPS IN ORGANIC SYNTHESIS and the like can be used.

The following will describe, as an example, a case of the protection with a benzyl group that is a suitable protective group but the step is not limited thereto.

In the case of the protection with the benzyl group, the protection can be carried out by reacting the compound represented by the formula (6) with a benzylation agent such as benzyl chloride or benzyl bromide and an alkali catalyst.

Since stirring efficiency decreases with no solvent owing to a high viscosity and thus benzylation efficiency decreases, the reaction is preferably carried out in a reaction solvent. The solvent is not particularly limited but includes aprotic solvents such as tetrahydrofuran, dimethyl ether, methylene chloride, chloroform, dimethylformamide, toluene, and benzene.

The amount of the benzylation agent is preferably 1.0 to 8.0 equivalents, more preferably 1.0 to 5.0 equivalents to the compound represented by the formula (6).

The alkali catalyst is not particularly limited but includes sodium hydroxide, potassium hydroxide, sodium, sodium hydride, calcium hydride, sodium methoxide, potassium methoxide, hexamethyldisilazane sodium, hexamethyldisilazane potassium, tert-butoxy sodium, and tert-butoxy potassium. Suitably, 1.0 to 3.0 molar equivalents of an alkali catalyst is added to the compound represented by the formula (6) and the reaction is carried out at 50 to 110° C. On this occasion, in order to induce the exchange reaction more easily, a pressure-reducing operation may be conducted. At a reaction temperature of 50° C. or lower, the reaction ratio of the exchange reaction decreases and the benzylation is not achieved. Moreover, at 110° C. or higher, there is a concern that the cyclic ketal structure is decomposed to form a hydroxyl group. Both impurities are protected and, after addition polymerization of an alkylene oxide, are deprotected to form impurities having a molecular weight smaller than that of the objective compound. In the case of the reaction with a bio-related substance, they cause a decrease in purity of the desired substance.

After the reaction, the compound represented by the formula (5) may be isolated by a purification means such as column chromatography, distillation, or supercritical extraction but the next step may be carried out without purification.

(Deketalization, Acid Hydrolysis)

As for deprotection of the cyclic ketal structure, the compound represented by the formula (5) is reacted in an aqueous solution adjusted to pH 1 to 4 with an acid such as acetic acid, phosphoric acid, sulfuric acid, or hydrochloric acid to achieve acid hydrolysis, thereby producing the compound represented by the formula (3).

The amount of the acid to be used is preferably set so that pH during the reaction becomes 1.0 to 4.0.

The reaction can be carried out in water or a mixed solvent of a water-soluble solvent and water. As the water-soluble solvent, for example, methanol, acetonitrile, or the like can be used.

The reaction temperature is usually 20 to 100° C., preferably 40 to 90° C. The reaction time is preferably 0.5 to 5 hours.

After the deketalization reaction, neutralization is carried out with an alkali such as sodium hydroxide, potassium hydroxide, sodium carbonate, or sodium acetate to obtain an aqueous solution containing the compound represented by the formula (3).

Step (B2): a step of repeatedly washing an aqueous solution obtained in the step (B1) with a water-insoluble organic solvent By the step, a fat-soluble impurity can be removed.

The amount of the water-insoluble organic solvent to be used is not particularly limited but is preferably 1 to 10 times by weight relative to the compound represented by the formula (5) used in the step (B1).

When the washing is insufficient, impurities in the desilylation and impurities in the protection step remain, they are reacted with an alkylene oxide to form impurities of functional group-introduced polyoxyalkylene compounds in the following or later step as the case of the objective compound. In the case of bonding to a bio-related substance, they become impurities of the bio-related substance and cause a decrease in purity, so that it is preferred to conduct the washing for a washing time of 10 minutes to 2 hours repeatedly.

The washing temperature is not particularly limited but the washing is preferably conducted at 5 to 50° C. At 5° C. or lower, the viscosity of the solution increases and removing efficiency becomes worse. Moreover, at 50° C. or higher, since the objective compound dissolves in an organic solvent, a yield obtained after completion of the step decreases and thus industrial productivity decreases.

As the water-insoluble organic solvent, chloroform, methylene chloride, ethyl acetate, tert-butyl methyl ether, and the like are preferred, and further, chloroform is preferred.

After the washing with the water-insoluble organic solvent, without particular limitation, the removal of inorganic salts from the aqueous layer is preferred. For the removal of the inorganic salts, active carbon, ion-exchange resins, and the like are preferred, and further, ion-exchange resins are preferred.

The ion-exchange resins include ion-exchange resins containing a sulfonic acid group or a carboxylic acid group as strongly acidic ion-exchange resins and ammonium ion-exchange resins containing a hydroxyl group as strongly basic ion-exchange resins. The strongly acidic ion-exchange resins and strongly basic ion-exchange resins are not particularly limited and may be treated individually or treated after mixing. The amount of the ion-exchange resin to be used is suitably 0.5 to 20 times, further 0.5 to 10 times relative to the compound represented by the formula (3). When the amount is less than 0.5, purification is insufficient and, when ionic components remain, side reactions such as terminal vinyl etherification occur at the time of alkylene oxide addition polymerization in the next step, so that the quality of the objective compound tends to decrease.

The compound represented by the formula (3) can be obtained by conducting concentration of the resulting aqueous layer, dehydrative drying by azeotropic removal of water with an organic solvent such as toluene, and the like.

(Alkylene Oxide Addition)

The alkylene oxide addition polymerization to the compound represented by the formula (3) having four hydroxyl groups which is newly formed by deprotection of the cyclic acetal structure is not particularly limited but preferably, production can be carried out through the following step (A1), subsequently steps (A2) and (A3).

Step (A1): a step of dissolving the compound represented by the formula (3) in an aqueous solution containing an alkali catalyst in 50% by mol to 150% by mol relative to the compound, adding an organic solvent, and conducting azeotropic removal of water preferably at 50 to 130° C.

Step (A2): a step of reacting an alkylene oxide with the compound represented by the formula (3) at 50 to 130° C. to obtain the compound represented by the formula (4)

Step (A3): on the compound represented by the above formula (4), a step of etherifying terminal hydroxyl groups of the polyoxyalkylenes and, after deprotection of $R^2$, introducing a group containing $L^1$ in the case where $L^1$ is not a single bond or an oxyalkylene into the terminal hydroxyl group in the case where n is 1 or more, thereby obtaining the compound represented by the formula (2)

Step (A4): a step of converting the hydroxyl group of the compound represented by the formula (2) into $-L^2-X$ Step (A1)

The alkali catalyst in the step (A1) is not particularly limited but includes metal sodium, metal potassium, sodium hydride, potassium hydride, sodium hydroxide, potassium hydroxide, sodium methoxide, potassium methoxide, and the like. The concentration of the alkali catalyst is preferably 50% by mol to 150% by mol. When the concentration is less than 50% by mol, the polymerization reaction rate of the alkylene oxide decreases and heat hysteresis increases to result in formation of impurities such as a terminal vinyl ether compound, so that the concentration of 50% by mol or more is advantageous in view of production of a high quality high-molecular-weight compound. When the concentration of the catalyst exceeds 150% by mol, the viscosity of the reaction liquid increases or the liquid solidifies at the time of the alcoholate-forming reaction to lower the stirring efficiency and there is a tendency that the alcoholate formation is not accelerated.

The organic solvent for the azeotropic removal of water is not particularly limited but includes methanol, ethanol, toluene, benzene, and xylene, and toluene having a boiling point similar to that of water is preferred. The azeotropic temperature is preferably 50 to 130° C. When the temperature is lower than 50° C., the viscosity of the reaction liquid increases and there is a tendency that water remains. The remaining of water forms a polyoxyalkylene compound derived from water and the compound may be mixed in as an impurity that is undesirable for pharmaceutical uses. Also, when the temperature is higher than 130° C., there is a concern that a condensation reaction occurs. In the case where water remains, it is preferred to conduct the azeotropic removal of water repeatedly.

Step (A2)

The step (A2) is carried out with no solvent or in an solvent. The reaction solvent is not particularly limited as far as it is an aprotic solvent such as toluene, benzene, xylene, acetonitrile, ethyl acetate, tetrahydrofuran, chloroform, methylene chloride, dimethyl sulfoxide, dimethylformamide, or dimethylacetamide but toluene or no solvent is preferred. The reaction time is preferably 1 to 24 hours. When the time is shorter than 1 hour, there is a concern that the catalyst is not completely dissolved. When the time is longer than 24 hours, there is a concern that the aforementioned decomposition reaction occurs.

The alkylene oxide includes ethylene oxide, propylene oxide, trimethylene oxide, 1-ethylethylene oxide, 1,2-dimethylethylene oxide, tetramethylene oxide, and the like. Preferred are ethylene oxide and propylene oxide and more preferred is ethylene oxide.

The reaction temperature is preferably 50 to 130° C. When the temperature is lower than 50° C., the polymerization reaction decreases and heat hysteresis increases, so that the quality of the compound represented by the formula (4) tends to decrease. Also, when the temperature is higher than 130° C., side reactions such as terminal vinyl etherification occurs during polymerization and thus there is a tendency that the quality of the objective compound decreases. As the molecular weight increases during polymerization, the viscosity of the reaction liquid increases, so that an aprotic solvent, suitably toluene may be added in an appropriate manner.

The step (A2) may be repeatedly carried out more than once before subjection to the step (A3). In that case, the step can be carried out in the same manner as the above-mentioned conditions by adding an alkylene oxide to the reaction mixture remaining in the reaction vessel. By adjusting the repeating times, the average number m of moles added can be adjusted.

Step (A3)
(Etherification)

For the alkyl etherification of the terminal hydroxyl group of the polyoxyalkylene of the compound represented by the formula (4), already known methods may be used but specifically, the following (A3-1) and (A3-2) may be mentioned.

(A3-1) a method of converting the terminal hydroxyl group of the polyoxyalkylene into an alcoholate and reacting it with an alkyl halide (A3-2) a method of activating the terminal hydroxyl group of the polyoxyalkylene with methanesulfonyl chloride, p-toluenesulfonyl chloride, 2,2,2-trifluoroethanesulfonyl chloride, or the like and reacting activated one with an alcoholate of an alkyl alcohol Suitable is the method of (A3-2). The following will describe the method in further detail but the step is not limited thereto.

The producing method of (A3-2) comprises the following steps (A3-2-1), (A3-2-2), and (A3-2-3).

Step (A3-2-1): a step of adding a tertiary amine and a compound represented by the formula (23) to the compound represented by the formula (4) and reacting them preferably at 20 to 60° C. to obtain a compound represented by the formula (24). On this occasion, molar ratios of respective charged compounds satisfy the following relations.

$$Vi \geq 5Vg$$

$$Vh > Vi$$

Vg: number of moles of the compound represented by the formula (4)
Vh: number of moles of the tertiary amine
Vi: number of moles of the compound represented by the formula (23)

More preferred is a case where relations:

$$25Vg \geq Vi \geq 5Vg$$

$$6Vi > Vh > Vi$$

are satisfied.

When Vi is smaller than 5Vg, there is a concern that the reaction ratio decreases and a hydroxyl group remains at an oxyalkylene chain terminal. A functional group is introduced into the remaining hydroxyl group in later steps to form a multifunctional impurity having the same molecular weight as that of the objective compound. When such a multifunctional impurity is present, it acts as a crosslinking agent at the time of bonding to a bio-related substance and the purity of the modified bio-related substance tends to decrease. Also, when Vh is equal to or smaller than Vi, since the acid produced as a by-product with the progress of the reaction cannot be efficiently trapped, the reaction ratio decreases and thus a hydroxyl group remains at the oxyalkylene chain terminal. Moreover, when Vi is larger than 25Vg and Vh is equal to or larger than 6Vi, the excessive amount may be mixed into later steps to cause a side reaction.

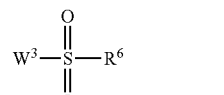
(23)

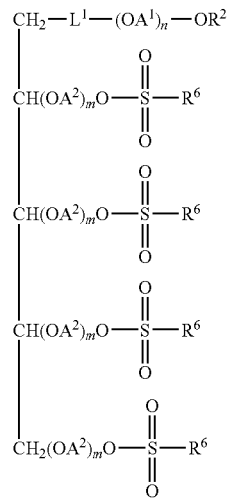
(24)

wherein $W^3$ is a halogen atom and $R^6$ represents a hydrocarbon group having 1 to 10 carbon atoms that may contain a fluorine atom or an alkoxy having 1 to 3 carbon atoms that may be substituted with a fluorine atom.

The above $R^6$ is a hydrocarbon group having 1 to 10 carbon atoms that may contain a fluorine atom or an alkoxy having 1 to 3 carbon atoms that may be substituted with a fluorine atom, and the hydrocarbon group includes linear or branched alkyl groups having 1 to 10 carbon atoms, linear or branched alkenyl groups having 2 to 10 carbon atoms, linear or branched alkynyl groups having 2 to 10 carbon atoms, aryl groups having 6 to 10 carbon groups, linear or branched arylalkyl groups having 7 to 10 carbon atoms, linear or branched arylalkenyl groups having 8 to 24 carbon atoms, linear or branched arylalkynyl groups having 8 to 24 carbon atoms, and linear or branched alkylaryls having 7 to 10 carbon atoms. Specifically, there may be mentioned a methyl group, an ethyl group, a propyl group, an isopropyl group, a butyl group, a tert-butyl group, a hexyl group, a nonyl group, a vinyl group, a phenyl group, a benzyl group, a 4-methylphenyl group, a trifluoromethyl group, a 2,2,2-trifluoroethyl group, 4-(trifluoromethoxy)phenyl group, and the like but preferred are cases of a methyl group, a vinyl group, a 4-methylphenyl group, and a 2,2,2-trifluoroethyl group.

The base to be used includes organic bases such as triethylamine, pyridine, and 4-dimethylaminopyridine, or inorganic bases such as sodium carbonate, sodium hydroxide, sodium hydrogen carbonate, sodium acetate, potassium carbonate, and potassium hydroxide but preferred bases are organic bases such as triethylamine, pyridine, and 4-dimethylaminopyridine.

Moreover, in the compound represented by the formula (23) to be used, $W^3$ represents the same group as mentioned above and is preferably Cl or Br. Also, $R^6$ is preferably a case of a methyl group, a phenyl group, or a p-methylphenyl group and, more suitably, methanesulfonyl chloride wherein $W^3$ is Cl and $R^6$ is a methyl group is most preferred.

The present step is preferably carried out in a solvent. The solvent to be used on this occasion is not particularly limited as far as it is an aprotic solvent but preferably includes toluene, benzene, xylene, acetonitrile, ethyl acetate, tetrahydrofuran, chloroform, methylene chloride, dimethyl sulfoxide, dimethylformamide, dimethylacetamide, and the like, and further preferred is toluene which can remove water in the reaction system by azeotropic removal of water. The amount of the solvent to be used at the reaction is preferably 0.5 time by weight to 10 times by weight relative to the compound represented by the formula (4). In the case where the molecular weight of the compound represented by the formula (4) is large, the viscosity of the reaction liquid increases and the reaction ratio decreases, so that it is preferred to dilute the liquid with a solvent.

The reaction temperature is not particularly limited but is preferably 60° C. or lower for suppressing the side reaction and is preferably 20° C. or higher in view of suppressing an increase in the viscosity of the reaction solution. The reaction time is preferably 1 to 24 hours. When the time is shorter than 1 hour, there is a concern that the reaction ratio is low. When the time is longer than 24 hours, there is a concern that the side reaction occurs.

At the reaction, an operation of removing water from a starting material such as azeotropic removal of water may be carried out prior to the reaction. Also, an antioxidant such as 2,6-di-tert-butyl-p-cresol may be added. Moreover, as the reaction proceeds and the compound represented by the formula (24) is formed, a salt is formed but, after completion of the reaction, it is possible to enter the next step without further operation or the salt may be removed by filtration or, after the filtration, the compound represented by the formula (24) may be purified by a purification means such as extraction, recrystallization, adsorption treatment, reprecipitation, column chromatography, or supercritical extraction.

Step (A3-2-2): a step of adding a compound represented by the formula (25) to the compound represented by the formula (24) and reacting them preferably at 20 to 80° C. to obtain the compound represented by the formula (10). On this occasion, molar ratios of respective charged compounds satisfy the following relation:

$$Vk>Vj$$

Vk: number of moles of the compound represented by the formula (25)

Vj: number of moles of the compound represented by the formula (24); More preferred is a case where a relation:

$$20Vj>Vk>Vj$$

is satisfied.

$$MO-R \quad (25)$$

In the compound represented by the above formula (25), R has the same meaning as that of $R^1$ or the like and M is sodium or potassium, suitably sodium.

When Vk is equal to or smaller than Vj, the etherification reaction does not sufficiently proceed and a reactive group such as a mesylate group remains at the oxyalkylene chain terminal. In the case where the reactive group remains at the oxyalkylene chain terminal, as mentioned above, it is converted into a multifunctional compound, which causes a serious side reaction at the time of bonding to the bio-related substance. Moreover, in the case where Vk is equal to or larger than 20Vj, an excessive alcoholate is mixed into later steps and causes a side reaction and the like.

The reaction is carried out preferably in a solvent. The solvent to be used is not particularly limited as far as it is the aforementioned aprotic solvent but preferred is toluene. The amount of the solvent to be used at the reaction is preferably 0.5 time to 10 times relative to the compound represented by the formula (24). In the case where the molecular weight of the compound represented by the formula (24) is large, the viscosity of the reaction liquid increases, so that it is preferred to dilute the solution with a solvent.

The reaction temperature is not particularly limited but is preferably 80° C. or lower for suppressing the side reaction and is preferably 20° C. or higher in view of suppressing an increase in the viscosity of the reaction liquid. The reaction time is preferably 1 to 24 hours. When the time is shorter than 1 hour, there is a concern that the reaction ratio is low. When the time is longer than 24 hours, there is a concern that the side reaction occurs. At the reaction, an operation of removing water from a starting material such as azeotropic removal of water may be carried out prior to the reaction.

Step (A3-2-3): a step of filtrating the reaction liquid or washing the reaction liquid with an aqueous inorganic salt solution having a concentration of 10% by weight or more.

The inorganic salt is not particularly limited in its kind but is suitably sodium chloride. When the concentration is less than 10% by weight, the objective compound migrates into the aqueous layer to lower a yield ratio remarkably. The operation of washing with water may be repeated more than once. The step (A3-2-3) is carried out for removing excessively added starting materials, salts produced as by-products, and the like. When the step is skipped, a side reaction may be caused in the case where the step (A3) is again carried out. In the case where a deprotection step is carried out as a next step, these impurities may act as catalyst poisons and influence the reaction ratio.

Moreover, in order to increase the etherification ratio of the polyoxyalkylene chain terminal, it is preferred to carry out the steps (A3-2-1) to (A3-2-3) repeatedly. When the alkyl etherification ratio of the polyoxyalkylene chain terminal is low, there is a concern that multifunctional impurities may be formed as mentioned above.

The compound represented by the formula (10) thus obtained may be purified by a purification means such as extraction, recrystallization, adsorption treatment, reprecipitation, column chromatography, or supercritical extraction.

The subsequent deprotection step is not particularly limited and known methods presented in PROTECTIVE IN ORGANIC SYNTHESIS and the like can be employed but, for example, in the case where $R^2$ is a benzyl group, the step can be carried out by the hydrogenation reaction of the following step (A3-3) using a hydrogenative reduction catalyst and a hydrogen donor. The following will describe the benzyl group step (A3-3) as one example but the present step is not limited thereto.

Step (A3-3)

As the hydrogenative reduction catalyst where $R^2$ is benzyl ether, palladium is preferred. The support is not particularly limited but is preferably alumina or carbon and is further preferably carbon. The amount of the catalyst is preferably 1 to 20% by weight relative to the compound represented by the formula (10). When the amount is less than 1% by weight, there is a concern that the deprotection ratio decreases and the functional group formation ratio at the following step decreases. Also, when the amount is larger than 20% by weight, there is a concern that the decomposition reaction of the polyoxyalkylene chain occurs and the aforementioned reactive low-molecular-weight compound is produced as a by-product.

The reaction solvent is not particularly limited but preferably includes methanol, ethanol, 2-propanol, and the like and further preferred is methanol.

The hydrogen donor is not particularly limited but includes hydrogen gas, cyclohexene, 2-propanol, and the like.

The reaction temperature is preferably 70° C. or lower and, when the temperature is higher than 70° C., there is a concern that the decomposition reaction of the polyoxyalkylene compound occurs and the reactive low-molecular-weight compound is formed.

The reaction time is not particularly limited. When the amount of the catalyst is large, the reaction is completed in a short period of time and, when the amount of the catalyst is small, it takes a long period of time, but preferred is 1 to 5 hours. When the time is shorter than 1 hour, there is a concern that the reaction ratio is low. When the time is longer than 5 hours, there is a concern that the decomposition reaction of the polyoxyalkylene compound occurs.

The compound represented by the formula (11) obtained may be purified by a purification means such as extraction, recrystallization, adsorption treatment, reprecipitation, column chromatography, or supercritical extraction.

The compound represented by the formula (11) thus obtained is a polyoxyalkylene compound containing substantially no secondary hydroxyl group.

Since the compound represented by the formula (11) contains substantially no secondary hydroxyl group, the reaction ratio of the subsequent functional group-introducing reaction is high and a polyoxyalkylene compound having a high purity can be obtained. In the case where a secondary hydroxyl group is present, the reaction ratio of introducing a functional group is low and the purity of an intermediate for a modified bio-related substance decreases, so that there is a possibility that an impurity is mixed into pharmaceuticals and the like and thus become problem.

Subsequently, in the case where $L^1$ is not a single bond, a group containing $L^1$ is introduced into the compound represented by the formula (11). For example, in the case where $L^1$ is —OC(=O)NH(CH$_2$)$_2$—, the introduction can be carried out together with the introduction of the polyoxyalkylene group according to the following step (3-4-2). Alternatively, in the case where $L^1$ is —OC(=O)NH— and n is zero, it can be introduced by reacting the compound represented by the formula (11) with N,N'-disuccinimidyl carbonate or p-nitrophenyl chloroformate to convert the hydroxyl group of the compound represented by the formula (11) into a succinimidyl carbonate group or a p-nitrophenyl carbonate group and subsequently reacting the resulting product with a corresponding amine compound (e.g., propargylamine, 1-amino-3,3-diethoxypropane, etc.). However, needless to say, the introduction is not limited thereto.

The subsequent introduction of a polyoxyalkylene group into the terminal hydroxyl group is not particularly limited but specifically, the following steps (A3-4-1) and (A3-4-2) may be mentioned.
Step (A3-4-1)
A method of achieving the introduction by reacting the compound represented by the formula (11), which is obtained by deprotection, with an alkylene oxide by the method of the step (A2)

Step (A3-4-2)
A step of converting the terminal hydroxyl group of the compound represented by the formula (11) obtained by deprotection into a reactive functional group, reacting the resulting product with an aminopolyoxyalkylene whose one terminal hydroxyl group is not protected or reacting the product with an aminopolyoxyalkylene protected with $R^2$, and subsequently deprotecting the protective group of $R^2$
Step (A3-4-2-1)
A method of obtaining the compound represented by the formula (2) by deprotection according to the method of the step (A3-3) in the case where one terminal hydroxyl group is protected with $R^2$.

The following will describe the step (A3-4-2).
(A3-4-2)
The reactive functional group is not particularly limited but specifically includes a p-nitrophenyl carbonate group and an N-hydroxysuccinimidyl carbonate group, and preferred is a p-nitrophenyl carbonate group.

The following will describe a case of conversion into the p-nitrophenyl carbonate group but the present step is not limited thereto.

With regard to the reaction, the conversion can be achieved by reacting an organic base such as triethylamine, pyridine, 4-dimethylaminopyridine or an inorganic base such as sodium carbonate, sodium hydroxide, sodium hydrogen carbonate, sodium acetate, potassium carbonate, or potassium hydroxide and any of compounds represented by the following general formula (b1) with the compound represented by the formula (11) in an aprotic solvent such as toluene, benzene, xylene, acetonitrile, ethyl acetate, diethyl ether, t-butyl methyl ether, tetrahydrofuran, chloroform, methylene chloride, dimethyl sulfoxide, dimethylformamide, or dimethylacetamide or with no solvent. Moreover, the above organic base and inorganic base may not be used. The ratio of the organic base and inorganic base to be used is not particularly limited but equimolar or more relative to the compound represented by the formula (11) obtained by deprotection is preferred. Also, an organic base may be used as a solvent. $W^1$ in the formula (b1) is a halogen atom (e.g., Cl, Br, I) and is preferably Cl. The ratio of the compound represented by the formula (b1) to be used is not particularly limited but is preferably equimolar or more relative to the compound represented by the formula (11) obtained by deprotection, and further preferably, it is preferred to react them in the range of equimolar to 50 molar. The reaction temperature is preferably 0 to 300° C., further preferably 20 to 150° C. The reaction time is preferably 10 minutes to 48 hours, further preferably 30 minutes to 24 hours. The compound formed may be purified by a purification means such as extraction, recrystallization, adsorption treatment, reprecipitation, column chromatography, or supercritical extraction.

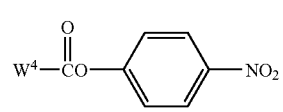

(b1)

wherein $W^4$ represents a halogen atom.

Subsequently, the reaction with the aminopolyoxyalkylene can be carried out in an aprotic solvent such as toluene, benzene, xylene, acetonitrile, ethyl acetate, diethyl ether, t-butyl methyl ether, tetrahydrofuran, chloroform, methylene chloride, dimethyl sulfoxide, dimethylformamide, or dimethylacetamide or with no solvent. The protective group for the one terminal hydroxyl group of the aminopolyoxyalkylene is a hydrocarbon group having 1 to 24 carbon atoms. Specific hydrocarbon group includes hydrocarbon groups such as a methyl group, an ethyl group, a propyl group, an isopropyl group, a butyl group, a tert-butyl group, a pentyl group, an isopentyl group, a hexyl group, a heptyl group, a 2-ethylhexyl group, an octyl group, a nonyl group, a decyl group, an undecyl group, a dodecyl group, a tridecyl group, a tetradecyl group, a pentadecyl group, a hexadecyl group, a heptadecyl group, an ocradecyl group, an oleyl group, a nonadecyl group, an eicosyl group, a heneicosyl group, a docosyl group, a tricosyl group, a tetracosyl group, a benzyl group, a cresyl group, a butylphenyl group, and a dodecylphenyl group. Preferred are cases of hydrocarbon groups having 1 to 10 carbon atoms, more preferred are cases of a tert-butyl group and a benzyl group, and further preferred is a case of a benzyl group. The reaction temperature is preferably 0 to 300° C., further preferably 20 to 150° C. The reaction time is preferably 10 minutes to 48 hours, further preferably 30 minutes to 24 hours. The compound formed may be purified by a purification means such as extraction, recrystallization, adsorption treatment, reprecipitation, column chromatography, or supercritical extraction.

The deprotection is not particularly limited but, in the case of deprotection of the benzyl group, specifically, the method of (A-3) may be mentioned.

The method of the conversion into the N-hydroxysuccinimidyl carbonate group can be conducted in the same manner as above except that N,N-disuccinimidyl carbonate is used instead of the compound represented by the above general formula (b1).

The compound represented by the formula (2) can be obtained by the above method but can be also obtained by the following step (D-1) or (D-2).

(D-1)

A method capable of obtaining the compound (2) by carrying out the above steps (A3-4-1), (B1), (B2), (A1), (A2), and (A3) sequentially using the compound represented by the formula (6)

(D-2)

A method capable of obtaining the compound (2) by carrying out the above steps (A3-4-2-1), (B1), (B2), (A1), (A2), and (A3) sequentially using the compound represented by the formula (6)

Step (A4)

The step of converting the hydroxyl group of the compound (2) into $-L^2-X$ will be described.

(Introducing Method of (b), (e))

(b) and (e) can be introduced by reacting the compound (2) with an organic base such as triethylamine, pyridine, 4-dimethylaminopyridine, hexamethyldisilazane sodium, or hexamethyldisilazane potassium or an inorganic base such as sodium carbonate, sodium hydroxide, sodium hydrogen carbonate, sodium acetate, potassium carbonate, potassium hydroxide, or sodium hydride and either of compounds represented by the following general formulae (b1) and (e1) or (e2), respectively, in an aprotic solvent such as toluene, benzene, xylene, acetonitrile, ethyl acetate, diethyl ether, t-butyl methyl ether, tetrahydrofuran, chloroform, methylene chloride, dimethyl sulfoxide, dimethylformamide, or dimethylacetamide or with no solvent. The ratio of the organic base and inorganic base to be used is not particularly limited but is preferably equimolar or more relative to the compound (2). Also, an organic base may be used as a solvent. $W^4$ in the general formulae (b1) and (e1) is a halogen atom (e.g., Cl, Br, I) and is preferably Cl. Moreover, $Y^3$ in the general formula (e1) is a hydrocarbon group having 1 to 10 carbon atoms that may contain a fluorine atom or an alkoxy having 1 to 3 carbon atoms that may be substituted with a fluorine atom and is preferably a methyl group, a 4-methylphenyl group, or a trifluoromethyl group. $Y^4$ in the general formula (e2) is a hydrocarbon group having 1 to 10 carbon atoms and is preferably a vinyl group or isopropenyl group. The ratio of the compound represented by the general formula (b1), (e1), or (e2) is not particularly limited but is preferably equimolar or more relative to the compound (2), and further preferably, it is preferred to react them in the range of equimolar to 50 molar. The reaction temperature is preferably 0 to 300° C., further preferably 20 to 150° C. The reaction time is preferably 10 minutes to 48 hours, further preferably 30 minutes to 24 hours. The compound formed (1) may be purified by a purification means such as extraction, recrystallization, adsorption treatment, reprecipitation, column chromatography, or supercritical extraction.

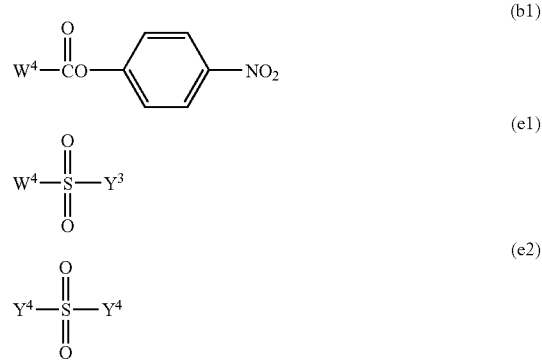

wherein $W^4$, $Y^3$, and $Y^4$ represent the same groups as mentioned above.

(Introducing Method of (f))

A carboxyl body (f) can be introduced by reacting the compound (2) with a dicarboxylic acid anhydride such as succinic anhydride or glutaric anhydride.

The reaction of the compound (2) with the dicarboxylic acid anhydride is carried out in the aforementioned aprotic solvent or with no solvent. The ratio of the dicarboxylic acid anhydride to be used is not particularly limited but is preferably equimolar or more, further preferably equimolar to 5 molar relative to the compound (2). The reaction temperature is preferably 0 to 200° C., further preferably 20 to 150° C. The reaction time is preferably 10 minutes to 48 hours, further preferably 30 minutes to 12 hours. For the reaction, an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide may be used as a catalyst. The ratio of the catalyst to be used is preferably 0.1 to 50% by weight, further preferably 0.5 to 20% by weight relative to the compound (2). The compound (1) containing the carboxyl body (f) thus formed may be purified by a purification means such as extraction, recrystallization, adsorption treatment, reprecipitation, column chromatography, or supercritical extraction or may be used as it is in the case where the compound is used as a starting material for the condensation reaction.

The compound (1) containing the carboxyl body (f) can be also obtained by the reaction with a haloalkylcarboxylic acid ester such as ethyl 6-bromohexanoate or ethyl 7-bromoheptanoate. The etherification of the compound (2) with the haloalkylcarboxylic acid ester is carried out in an aprotic solvent mentioned above or with no solvent. The ratio of the halogenated alkyl ester to be used is not particularly limited but is preferably equimolar or more, further preferably equimolar to 30 molar relative to the compound (2). The reaction temperature is preferably 0 to 200° C., further preferably 20 to 150° C. The reaction time is preferably 10 minutes to 48 hours, further preferably 30 minutes to 12 hours. For the reaction, an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide may be used as a catalyst. The ratio of the catalyst to be used is preferably 0.1 to 500% by weight, further preferably 0.5 to 300% by weight. After etherification, hydrolysis of the ester is carried out by adding an aqueous solution of sodium hydroxide, potassium hydroxide, or the like in the case of organic bases or water in the case of inorganic bases. The reaction temperature is preferably 0 to 100° C., further preferably 20 to 100° C. The reaction time is preferably 10 minutes to 48 hours, further preferably 30 minutes to 12 hours. After the reaction, neutralization with hydrochloric acid, sulfuric acid, or the like is carried out. The compound (1) containing the carboxyl body (f) thus formed may be purified by a purification means such as extraction, recrystallization, adsorption treatment, reprecipitation, column chromatography, or supercritical extraction or may be used as it is in the case where the compound is used as a starting material for the condensation reaction.

(Introducing Method of (a))

The compound (1) containing a succinimide body of (a) can be obtained by a condensation reaction of the compound (1) containing the carboxyl body (f) with N-hydroxysuccinimide in the presence of a condensation agent such as DCC or EDC. The condensation reaction is also carried out in the above aprotic solvent or with no solvent. The condensation agent is not particularly limited but is preferably DCC. The ratio of the condensation agent is preferably equimolar or more, further preferably equimolar to 5 molar relative to the compound (1) for the carboxyl body (f). The ratio of N-hydroxysuccinimide to be used is preferably equimolar or more, further preferably equimolar to 5 molar relative to the compound (1) for the carboxyl body (f). The reaction temperature is preferably 0 to 100° C., further preferably 20 to 80° C. The reaction time is preferably 10 minutes to 48 hours, further preferably 30 minutes to 12 hours. The compound formed may be purified by a purification means such as extraction, recrystallization, adsorption treatment, reprecipitation, column chromatography, or supercritical extraction.

Moreover, the compound (1) containing the succinimide body (a) can be also obtained by reacting the compound (2), N,N'-disuccinimide carbonate, and an organic base such as triethylamine, pyridine, 4-dimethylaminopyridine, hexamethyldisilazane sodium, or hexamethyldisilazane potassium. The reaction is also carried out in an aprotic solvent or with no solvent as in the above reaction. The ratio of the N,N'-disuccinimide carbonate to be used is preferably equimolar or more, further preferably equimolar to 20 molar relative to the compound (2). The reaction temperature is preferably 0 to 100° C., further preferably 20 to 80° C. The ratio of the organic base to be used is not particularly limited but is preferably equimolar or more relative to the compound (2). The reaction time is preferably 10 minutes to 48 hours, further preferably 30 minutes to 12 hours. The compound formed may be purified by a purification means such as recrystallization, adsorption treatment, reprecipitation, column chromatography, or supercritical extraction.

(Introducing Method of (k))

The compound (1) containing an amine body of (k) can be obtained by adding the compound (2) to acrylonitrile or the like in a solvent such as water or acetonitrile using an inorganic base such as sodium hydroxide or potassium hydroxide as a catalyst to obtain a nitrile body and subsequently carrying out a hydrogenation reaction of the nitrile group in the presence of nickel or palladium catalyst in an autoclave. The ratio of the inorganic base to be used at the time of obtaining the nitrile body is not particularly limited but is preferably 0.01 to 50% by weight relative to the compound (2). The ratio of acrylonitrile or the like to be used is not particularly limited but is preferably 0.5 to 5 times by weight relative to the weight of the compound (2) and further preferably, it is more preferred to carry out the reaction in the range of 1 to 4 times by weight. Also, acrylonitrile may be used as a solvent. The reaction temperature is preferably -50 to 100° C., further preferably –20 to 60° C. The reaction time is preferably 10 minutes to 48 hours, further preferably 30 minutes to 24 hours. The reaction solvent in the subsequent hydrogenation reaction of the nitrile body is not particularly limited as far as it is a solvent that is not involved in the reaction, but is preferably toluene. The ratio of the nickel or palladium catalyst to be used is not particularly limited but is 0.05 to 30% by weight, preferably 0.5 to 20% by weight relative to the nitrile body. The reaction temperature is preferably 20 to 200° C., further preferably 50 to 150° C. The reaction time is preferably 10 minutes to 48 hours, further preferably 30 minutes to 24 hours. The hydrogen pressure is preferably 2 to 10 MPa, further preferably 3 to 8 MPa. Moreover, in order to prevent dimerization, ammonia maybe added into the reaction system. The ammonia pressure in the case of adding ammonia is not particularly limited but is 0.1 to 10 MPa, further preferably 0.3 to 2 MPa. The compound formed may be purified by the aforementioned purification means.

The above compound (1) containing the amine body (k) can be also obtained by reacting the compound (1) containing (e) with aqueous ammonia. The reaction is carried out in aqueous ammonia. The concentration of ammonia is not particularly limited but is preferably in the range of 10 to 40%. The ratio of aqueous ammonia to be used is preferably 1 to 300 times relative to the weight of the compound (1) containing (e). The reaction temperature is preferably 0 to 100° C., further preferably 20 to 80° C. The reaction time is preferably 10 minutes to 72 hours, further preferably 1 hour to 36 hours. Also, the compound (1) containing the amine body (k) can be also obtained by reacting the compound (1) containing (e) with ammonia in an autoclave. The reaction solvent is not particularly limited but preferably includes methanol or ethanol. The amount of ammonia is preferably 10 to 300% by weight, further preferably 20 to 200% by weight relative to the compound (1) containing (e). The reaction temperature is preferably 50 to 200° C., further preferably 80 to 150° C. The reaction time is preferably 10 minutes to 24 hours, further preferably 30 minutes to 12 hours. The compound formed may be purified by the aforementioned purification means.

(Introducing Method of (l))

can be obtained by reacting the compound (1) containing the carbonate body (b) with the following compound (11) in the presence of an alkali catalyst such as triethylamine or pyridine.

A phthalimide body (12):

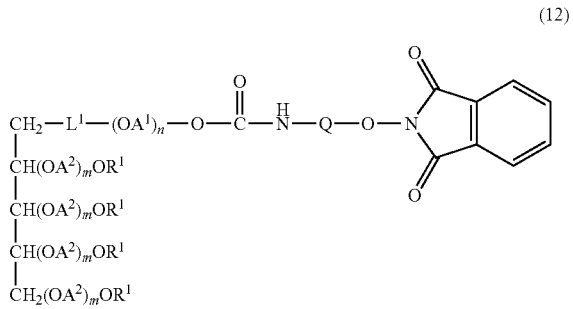

The reaction solvent is not particularly limited as far as it is no solvent or a polar solvent but is preferably methanol. The ratio of the alkali catalyst to be used is not particularly limited but is preferably equimolar or more relative to the compound (1) containing (b), and further preferably, the reaction is more preferably carried out in the range of equimolar to 20 molar. The ratio of the compound (11) to be used is preferably equimolar or more, further preferably equimolar to 20 molar relative to the compound (1) containing (b). The reaction temperature is preferably 0 to 100° C., further preferably 20 to 80° C. The reaction time is preferably 10 minutes to 48 hours, further preferably 30 minutes to 12 hours. The compound formed may be purified by a purification means such as extraction, recrystallization, adsorption treatment, reprecipitation, column chromatography, or supercritical extraction or may be subjected to the next step without purification.

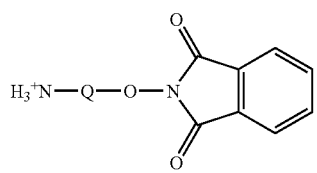

wherein Q represents the same group as mentioned below.

The compound (1) containing an oxyamine (1) can be obtained by reacting the above phthalimide body (12) in the presence of a multifunctional amine such as hydrazine or ethylenediamine.

The reaction solvent is not particularly limited but is preferably N,N-dimethylformamide or methylene chloride. The ratio in the presence of the multifunctional amine to be used is not particularly limited but is preferably equimolar or more relative to the compound (12), and further preferably, the reaction is more preferably carried out in the range of equimolar to 50 molar. The reaction temperature is preferably 0 to 100° C., further preferably 20 to 80° C. The reaction time is preferably 10 minutes to 48 hours, further preferably 30 minutes to 12 hours. The compound formed may be purified by a purification means such as extraction, recrystallization, adsorption treatment, reprecipitation, column chromatography, or supercritical extraction.

(Introducing Method of (d))

The compound (1) containing a maleimide body (d) can be obtained by reacting the compound (1) containing the amine (k) obtained by the aforementioned method with maleic anhydride in an aprotic solvent mentioned above or with no solvent to obtain a maleamide body and subsequently subjecting the product to a ring-closing reaction using acetic anhydride and sodium acetate as catalysts. The ratio of the maleic anhydride to be used in the maleamidation reaction is not particularly limited but is preferably equimolar or more, further preferably equimolar to 5 molar relative to the compound (1) containing (k). The reaction temperature is preferably 0 to 200° C., further preferably 20 to 120° C. The reaction time is preferably 10 minutes to 48 hours, further preferably 30 minutes to 12 hours. The maleamide body formed may be purified by the aforementioned purification means or may be used as it is in the next ring-closing reaction.

The reaction solvent in the subsequent ring-closing reaction is not particularly limited but is preferably an aprotic solvent or acetic anhydride. The ratio of the acetic anhydride to be used is not particularly limited but is preferably equimolar or more, further preferably equimolar to 50 molar relative to the maleamide body. The reaction temperature is preferably 0 to 200° C., further preferably 20 to 150° C. The reaction time is preferably 10 minutes to 48 hours, further preferably 30 minutes to 12 hours. The compound formed may be purified by the aforementioned purification means.

The above maleimide body can be also obtained by reacting the following general formula (d1) with the aforementioned compound (1) containing the amine (k). The reaction is carried out in an aprotic solvent mentioned above or with no solvent and the reaction is carried out with adding the compound (d1) in a ratio of equimolar or more relative to the compound (1) containing the amine (k). The ratio of the compound (d1) to be used is preferably equimolar or more, further preferably equimolar to 5 molar relative to the compound (1) containing (k). The reaction temperature is preferably 0 to 200° C., further preferably 20 to 80° C. The reaction time is preferably 10 minutes to 48 hours, further preferably 30 minutes to 12 hours. Light may be shielded at the time of the reaction. The compound formed may be purified by the aforementioned purification means.

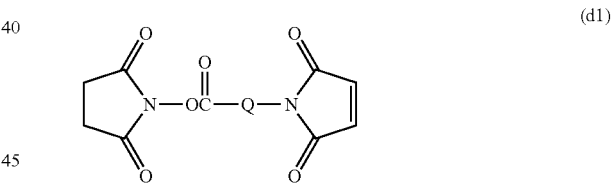

wherein Q represents a divalent hydrocarbon group having 1 to 7 carbon atoms.

As Q, there may be mentioned preferably a methylene group, an ethylene group, and a propylene group, further preferably an ethylene group and a propylene group.

(Introducing Method of (c))

The compound (1) containing an aldehyde body (c) can be obtained by reacting the compound (e) with an acetal compound represented by the following compound (c1) to obtain an acetal body and subsequently carrying out hydrolysis under an acidic condition. The production of the compound (1) containing (c) is as follows. The acetalization reaction can be carried out by reacting the compound (2) with the compound (c1) in a ratio of equimolar or more, preferably equimolar to 50 molar in the aforementioned solvent or with no solvent. The compound (c1) can be prepared from a corresponding alcohol using metal sodium, metal potassium, sodium hydride, potassium hydride, sodium methoxide, potassium t-butoxide, or the like. The reaction temperature is preferably 0 to 300° C., further preferably 20 to 150° C. The reaction time is preferably 10 minutes to 48 hours, further preferably 30 minutes to 24 hours.

In the case of using the following compound (c2), an acetal body can be obtained by converting the hydroxyl group of the compound (2) into an alcoholate by the aforementioned method and subsequently reacting the compound (c2) in a ratio of equimolar or more, preferably equimolar to 100 molar relative to the compound (2) in the aforementioned aprotic solvent or with no solvent. The reaction temperature is preferably 0 to 300° C., further preferably 20 to 150° C. The reaction time is preferably 10 minutes to 48 hours, further preferably 30 minutes to 24 hours.

In the case of using the following compound (c3), an acetal body can be obtained by reacting the compound (1) containing (a), (b), (e), or (f) with the compound (c3). The production of the compound (1) containing (a), (b), (e), or (f) is as mentioned above. In the reaction with the compound (c3), the solvent is not particularly limited but the reaction is preferably carried out in the aforementioned aprotic solvent. The ratio of the compound (c3) to be charged relative to the compound (1) containing (a), (b), (e), or (f) is preferably equimolar or more, further preferably equimolar to 10 molar. The reaction temperature is preferably −30 to 200° C., further preferably 0 to 150° C. The reaction time is preferably 10 minutes to 48 hours, further preferably 30 minutes to 24 hours. In the case of using the compound (1) containing (f), a condensation agent such as DCC or EDC may be suitably used. All the acetalization reactions may be carried out with light shielding. The acetal body thus obtained may be purified by the aforementioned purification means or may be used as it is in the next aldehyde-forming reaction without purification.

With regard to the aldehyde formation, the production can be carried out by transforming the acetal body to a 0.1 to 50% aqueous solution and hydrolyzing it in the aqueous solution whose pH is adjusted to 1 to 4 with an acid such as acetic acid, phosphoric acid, sulfuric acid, or hydrochloric acid.

The reaction temperature is preferably −20 to 100° C., further preferably 0 to 80° C.

The reaction time is preferably 10 minutes to 24 hours, further preferably 30 minutes to 10 hours. The reaction may be carried out with light shielding. The compound formed may be purified by the aforementioned purification means.

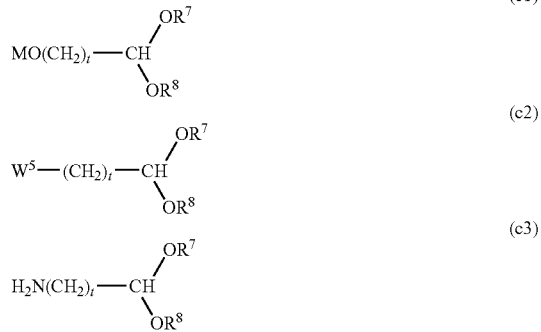

wherein $R^7$ and $R^8$ are a hydrocarbon group having 1 to 3 carbon atoms and may be the same or different from each other or they may be form a ring each other; M is sodium or potassium, $W^5$ is a halogen atom, and t is an integer of 1 to 5.

As $R^7$ and $R^8$, there may be mentioned preferably a methyl group, an ethyl group, and a propyl group, further preferably a methyl group and an ethyl group.

(Introducing Method of (g))

The compound (1) containing a mercapto body (g) can be obtained by reacting the compound (1) containing (e) with a thialation agent such as thiourea. The production of the compound (1) containing (e) is as follows. The thialation reaction is carried out in a solvent such as water, an alcohol, or acetonitrile or with no solvent. The ratio of the thialation agent to be used is preferably equimolar or more, further preferably in the range of equimolar to 50 molar relative to the compound (1) containing (e). The reaction temperature is preferably 0 to 300° C., further preferably 20 to 150° C. The reaction time is preferably 10 minutes to 48 hours, further preferably 30 minutes to 24 hours. After the reaction, the compound (1) containing the mercapto body can be obtained by subjecting the formed thiazolium salt to alkali hydrolysis. The compound formed may be purified by the aforementioned purification means.

Moreover, the above compound (1) containing the mercapto body can be also obtained by reacting the compound (1) containing (e) with the following compound (g1) and decomposing the product with a primary amine. The reaction of the compound (1) containing (e) with the compound (g1) is carried out in the aforementioned aprotic solvent or with no solvent. The ratio of the compound (g1) to be used is preferably equimolar or more, further preferably in the range of equimolar to 50 molar relative to the compound (1) containing (e). The reaction temperature is preferably 0 to 300° C., further preferably 20 to 80° C. The reaction time is preferably 10 minutes to 48 hours, further preferably 30 minutes to 24 hours. The subsequent alkali decomposition with a primary amine is carried out in the aforementioned solvent or with no solvent. The primary amine to be used is not particularly limited but preferably includes ammonia, methylamine, ethylamine, propylamine, butylamine, pentylamine, hexylamine, cyclohexylamine, ethanolamine, propanolamine, butanolamine, and the like. As a matter of course, these primary amines may be used as solvents. The compound formed may be purified by the aforementioned purification means.

(Introducing Method of (h))

The compound (1) containing (h) can be obtained by reacting the compound (1) containing (g) with 2,2-dipyridyl disulfide. In the reaction, the solvent is not particularly limited but the reaction is preferably carried out in an alcohol. The ratio of 2,2-dipyridyl disulfide to be charged relative to the compound (1) containing (g) is preferably equimolar or more, further preferably equimolar to 50 molar relative to the compound (1) containing (g). The reaction temperature is preferably −30 to 100° C., further preferably 0 to 60° C. The reaction time is preferably 10 minutes to 48 hours, further preferably 30 minutes to 24 hours. The compound (1) containing (h) thus obtained may be purified by the aforementioned purification means.

(Introducing Method of (i))

The compound (1) containing (i) can be obtained by reacting the compound (1) containing the amine (k) obtained by the method as mentioned above with iodoacetic anhydride in the aforementioned aprotic solvent or with no solvent. The ratio of iodoacetic anhydride to be used is not particularly limited but is preferably equimolar or more, further preferably equimolar to 5 molar relative to the compound (1) containing (k). The reaction temperature is preferably 0 to 200° C., further preferably 20 to 120° C. The reaction time is preferably 10 minutes to 48 hours, further preferably 30 minutes to 12 hours. The compound (1) containing (i) formed may be purified by a purification means such as extraction, recrystallization, adsorption treatment, reprecipitation, column chromatography, or supercritical extraction.

Moreover, the compound (1) containing (i) can be obtained by a condensation reaction of the compound (1) containing the amine (k) with iodoacetic acid in the presence of a condensation agent such as DCC or EDC. The condensation reaction is also carried out in a similar manner in the aforementioned aprotic solvent or with no solvent. The condensation agent is not particularly limited but is preferably DCC. The ratio of the condensation agent to be used is preferably equimolar or more, further preferably equimolar to 5 molar relative to the compound (1) containing (k). The ratio of iodoacetic acid to be used is preferably equimolar or more, further preferably equimolar to 5 molar relative to the compound (1) containing (k). The reaction temperature is preferably 0 to 100° C., further preferably 20 to 80° C. The reaction time is preferably 10 minutes to 48 hours, further preferably 30 minutes to 12 hours. The compound formed may be purified by the aforementioned purification means.

(Introducing Method of (m))

The compound (1) containing (m) can be obtained by reacting the compound (1) containing (a) obtained by the method as mentioned above with tert-butyl carbazinate in the presence of a base catalyst such as triethylamine or dimethylaminopyridine in the aforementioned aprotic solvent or with no solvent and subsequently carrying out a deprotection reaction. The ratio of tert-butyl carbazinate to be used is not particularly limited but is preferably equimolar or more, further preferably equimolar to 5 molar relative to the compound (1) containing (a). The ratio of the base catalyst to be used is not particularly limited but is preferably equimolar or more, further preferably equimolar to 7 molar relative to the compound (1) containing (a). The reaction temperature is not particularly limited but is preferably 0 to 100° C., further preferably 30 minutes to 12 hours. The tert-butyl hydrazide body thus obtained may be purified by the aforementioned purification means or may be used as it is in the next deprotection reaction without purification. As for the deprotection reaction, the production can be carried out by transforming the tert-butyl hydrazide body to a 0.1 to 50% aqueous solution and hydrolyzing it in the aqueous solution whose pH is adjusted to 1 to 4 with an acid such as acetic acid, phosphoric acid, sulfuric acid, or hydrochloric acid. The reaction temperature is preferably −20 to 100° C., further preferably 30 minutes to 10 hours. The compound formed may be purified by the aforementioned purification means.

(Introducing Method of (j))

The compound (1) containing an acetylene (j) can be obtained by reacting the compound (1) containing (a), (b), (c), or (e) with an acetylene compound represented by the following general formula (j1). The production of the compound (1) containing (a), (b), (c), or (e) is as mentioned above. The acetylene-forming reaction can be accomplished by reacting the compound (j1) in a ratio of equimolar or more, preferably equimolar to 50 molar relative to the compound (1) containing (a), (b), (c), or (e) in a protic solvent or with no solvent. The reaction temperature is preferably 0 to 300° C., further preferably 20 to 150° C. The reaction time is preferably 10 minutes to 48 hours, further preferably 30 minutes to 24 hours. The compound formed may be purified by the aforementioned purification means.

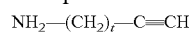  (j1)

wherein t is an integer of 1 to 5.

(Introducing Method of (n))

The compound (1) containing an azide (n) can be obtained by reacting the compound (1) containing (e) with sodium azide. The azide-forming reaction can be accomplished by reacting the compound (1) containing (e) with sodium azide in a ratio of equimolar or more, preferably equimolar to 50 molar in a protic solvent or with no solvent. The reaction temperature is preferably 0 to 300° C., further preferably 20 to 150° C. The reaction time is preferably 10 minutes to 48 hours, further preferably 30 minutes to 24 hours. The compound formed may be purified by the aforementioned purification means.

According to the invention, there is provided a multibranched polyoxyalkylene compound (1) which improves conventional viscosity in the same molecular weight and has four chains formed with an ether bond.

EXAMPLES

The following will describe the invention more specifically based on Examples. In this regard, $^1$H-NMR, GPC, or TOF-MS was employed for analyzing and identifying the compounds in Examples.

The molecular weight of polyoxyalkylene compounds was determined by TOF-MS analysis.

In the case where m and/or n are present in the structural formulae in the following compounds of Examples, the numerals of m and/or n were calculated from an equation where a mathematical formula expressing the molecular weight of each compound of Example or a starting material using m and/or n as variables is positioned as a left side and a molecular weight determined by the TOF-MS analysis is position as a right side.

<Method for $^1$H-NMR Analysis>

At $^1$H-NMR analysis, JNM-ECP400 and JNM-ECA600 manufactured by Nippon Denshi Datum K.K were employed. The integral values in NMR data are theoretical values.

<Method for GPC Analysis>

At GPC analysis, SHIMADZU LC-10Avp was employed as a GPC system and measurement was conducted under the following conditions: SHIMADZU LC-10Avp Developing solvent: dimethylformamide; flow rate: 0.7 ml/min; column: PL gel MIXED-Dx2 (Polymer Laboratory); column temperature: 65° C.; detector: RI; sample amount: 1 mg/g, 100 μl.

For GPC data, Mn means number average molecular weight, Mw means weight average molecular weight, an Mp means peak top molecular weight.

<Analytical Method for TOF-MS Analysis>

At TOF-MS analysis, Bruker autoflex III was employed.

Preparation of a measuring sample was carried out as follows:

A sample was dissolved in a THF solution prepared from 1,8,9-anthracenetriol and sodium trifluoroacetate to prepare a measuring sample.

Example 1-1

Synthesis of compound (p) (case of $R^1$=methyl group, $OA^1$, $OA^2$=oxyethylene group, n=0, and molecular weight=about 40000)

Example 1-1

In a 5 L round-bottom flask fitted with a thermometer, a nitrogen-introducing tube, and a stirrer were placed 1000 g of xylitol, 1916 g of 2,2-dimethoxypropane, and 37.5 mg of p-toluenesulfonic acid monohydrate. With introduction of nitrogen thereinto, the reaction was carried out at 65° C. The solvent of the reaction liquid was removed by evaporation and purification by distillation (b.p. 108° C./0.15 mmHg) was conducted to obtain an isomer mixture of 1,2,3,4-diisopropylidenexylitol and 1,2,4,5-diisopropylidenexylitol $^1$H-NMR (CDCl$_3$, internal standard TMS) δ (ppm): 1.37, 1.39, 1.44 (12H, s, —CH$_3$), 3.59-3.65 (1H, m, —CH—O—), 3.81-3.90 (2H, m, —CH$_2$—O—), 3.98-4.01 (1H, m, —CH—O—), 4.04-4.10 (2H, m, —CH$_2$—O—), 4.11-4.23 (1H, m, —CH—O—)

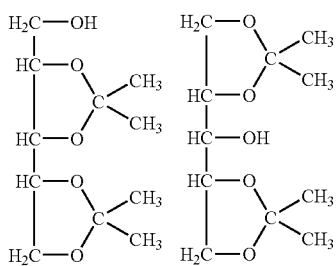 [SMILES: CC1(C)OCC(C2OC(C)(C)OC2CO)O1 ; CC1(C)OCC(C(O)C2COC(C)(C)O2)O1]

Example 1-2

In a 2 L round-bottom flask fitted with a thermometer, a nitrogen-introducing tube, and a stirrer were placed 250 g of diisopropylidenexylitol (isomer mixture) purified in 1-1, 1000 g of dichloromethane, 26 g of 4-dimethylaminopyridine, and 109 g of triethylamine. With introduction of nitrogen thereinto, the whole was dissolved at room temperature and, after cooling to 10° C. or lower, 297 g of t-butylchlorodiphenylsilane was added dropwise. After the dropwise addition, the temperature was returned to room temperature and the reaction was carried out for 2 hours. Thereafter, the mixture was washed with adding a saturated aqueous sodium hydrogen carbonate solution. After drying over magnesium sulfate, the solvent was removed by evaporation and 1,2,4,5-diisopropylidenexylitol was removed at 135° C. under reduced pressure (0.15 mmHg) to obtain 1,2,3,4-diisopropylidene-5-(t-butyldiphenylsilyl)xylitol.

$^1$H-NMR (CDCl$_3$, internal standard TMS) δ (ppm): 1.06 (9H, m, —Si—C—(CH$_3$)$_3$), 1.37, 1.42, 1.43 (12H, s, —O—C—CH$_3$), 3.72-3.82 (1H, m, —CH—O—, —CH$_2$—O—), 3.95 (1H, dd, —CH—O—), 3.99-4.06 (2H, m, —CH$_2$—O—), 4.11-4.15 (1H, m, —CH—O—), 7.36-7.54 (6H, m, Ph-Si(-Ph)-O—), 7.66-7.70 (4H, m, Ph-Si(-Ph)-O—)

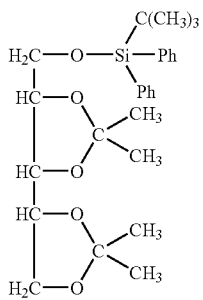

Example 1-3

In a 2 L round-bottom flask fitted with a thermometer, a nitrogen-introducing tube, and a stirrer were placed 500 g of 1,2,3,4-diisopropylidene-5-(t-butyldiphenylsilyl)xylitol obtained in 1-2 and 440 g of anhydrous tetrahydrofuran. With introduction of nitrogen thereinto, the whole was homogenized at room temperature and, after cooling to 20° C. or lower, 1270 ml of tetrabutylammonium fluoride (1 mol/L tetrahydrofuran solution) was added dropwise. After the dropwise addition, the temperature was returned to room temperature and the reaction was carried out for 2 hours. Thereafter, the solvent was removed by evaporation under reduced pressure. After the residue was dissolved with 2000 g of ethyl acetate, the ethyl acetate layer was washed with purified water and dried over magnesium sulfate. Then, the solvent was removed by evaporation to obtain 1,2,3,4-diisopropylidenexylitol.

$^1$H-NMR (CDCl$_3$, internal standard TMS) δ (ppm): 1.39, 1.44 (12H, s, —CH$_3$), 3.62 (1H, dd, —CH—O—), 3.08-3.89 (2H, m, —CH$_2$—O—), 3.98-4.08 (1H, m, —CH—O—, 2H, m, —CH$_2$—O—), 4.18-4.23 (1H, m, —CH—O—)

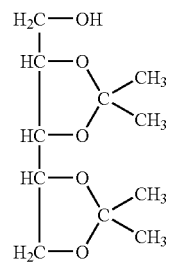

Example 1-4

In a 2 L round-bottom flask fitted with a thermometer, a nitrogen-introducing tube, a stirrer, a Dean-stark tube, and a condenser tube were placed 246 g of 1,2,3,4-diisopropylidenexylitol obtained in 1-3, 9848 g of toluene, and 1665 g of t-butoxy potassium. With introduction of nitrogen thereinto, water was removed at refluxing temperature and, after cooling to 80° C. or lower, 2013 g of benzyl chloride was added dropwise. After the dropwise addition, the reaction was carried out at 80° C. for 2 hours. Then, the organic layer was washed four times with 984 g of a 15% aqueous sodium chloride solution and the solvent was removed by evaporation to obtain 1,2,3,4-diisopropylidene-5-benzylxylitol.

$^1$H-NMR (CDCl$_3$, internal standard TMS) δ (ppm): 1.37, 1.40, 1.42, 1.44 (12H, s, —O—C—CH$_3$), 3.59 (2H, d, —CH$_2$—O—), 3.08 (1H, dd, —CH—O—), 3.91 (1H, dd, —CH—O—), 3.99 (1H, m, —CH—O—), 4.09 (2H, m, —CH$_2$—O—), 4.56 (2H, m, —O—CH$_2$-Ph), 7.22-7.39 (5H, m, —O—CH$_2$-Ph)

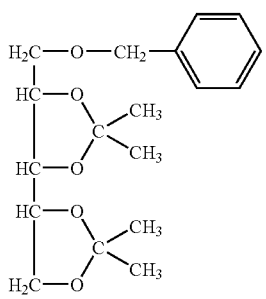 [SMILES: CC1(C)OCC(C2OC(C)(C)OC2COCc2ccccc2)O1]

Example 1-5

In a 5 L round-bottom flask fitted with a thermometer, a nitrogen-introducing tube, a stirrer, a Dean-stark tube, and a condenser tube were placed whole amount of 1,2,3,4-diisopropylidene-5-benzylxylitol obtained in 1-4 and water, and the aqueous solution was adjusted to pH 1.9 with adding an appropriate amount of phosphoric acid. After the adjustment, with introduction of nitrogen thereinto, the reaction was carried out at 70° C. for 2 hours. Then, the mixture was neutralized with an aqueous sodium hydroxide solution at room temperature and the aqueous layer was washed twice with 686 g of chloroform. The aqueous layer was charged into a column packed with DIAION SMN-1 (480 g) manufactured by Mitsubishi Chemical Corporation and eluted with ion-exchange water, and the aqueous layer was concentrated to obtain 1-benzylxylitol.

$^1$H-NMR (D$_2$O, internal standard TMS) δ (ppm): 3.45-3.63 (6H, m, —CH—CH$_2$—O—), 3.67-3.81 (1H, m, —CH—O—), 4.47 (2H, d, —O—CH$_2$-Ph), 7.25-7.34 (5H, m, —O—CH$_2$-Ph)

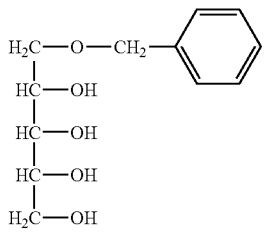 [SMILES: OCC(O)C(O)C(O)COCc1ccccc1]

Example 1-6

Into a 100 ml beaker containing 23.7 g of methanol and 6.8 g of water was charged 3.4 g of potassium hydroxide, which was dissolved at room temperature. After dissolution, the prepared potassium hydroxide solution and 18.0 g (0.07 mol) of the compound obtained in the above 1-5 were added to a 5 L autoclave and, after stirring at room temperature for 15 minutes, 180 g of toluene was charged thereinto. With introduction of nitrogen thereinto, the whole was treated at 105 to 110° C. to recover 180 g of water, methanol, and toluene and then was cooled to 50° C. or lower. Then, 180 g of anhydrous toluene was charged thereinto and, with introduction of nitrogen thereinto, the whole was treated at 105 to 110° C. to recover 120 g of water, methanol, and toluene. The inside of the autoclave system was replaced by nitrogen, temperature was elevated to 100° C., and 122 g (2.7 mol) of ethylene oxide was added thereto at 80 to 150° C. under a pressure of 1 MPa or less, followed by continuation of the reaction for another 1 hour. Toluene in the 5 L autoclave was removed under reduced pressure, temperature was elevated to 100° C., and 2662 g (60.5 mol) of ethylene oxide was added thereto at 80 to 150° C. under a pressure of 1 MPa or less, followed by continuation of the reaction for another 1 hour. After unreacted ethylene oxide gas was removed under reduced pressure, the whole was cooled to 60° C. and pH was adjusted to 7.5 with a 85% aqueous phosphoric acid solution to obtain the following compound (p1).

$^1$H-NMR (CDCl$_3$, internal standard TMS) δ (ppm): 3.40-3.80 (3623H, m, —CH$_2$O (CH$_2$CH$_2$O)$_m$H, CHO(CH$_2$CH$_2$O)$_m$H, CH$_2$OCH$_2$Ph), 4.48-4.57 (2H, m, —CH$_2$Ph), 7.27-7.38 (5H, m, —CH$_2$Ph)

GPC analysis; number average molecular weight (Mn): 37839, weight average molecular weight (Mw): 39503, polydispersity (Mw/Mn): 1.044, peak top molecular weight (Mp): 39669

TOF-MS analysis: 43440

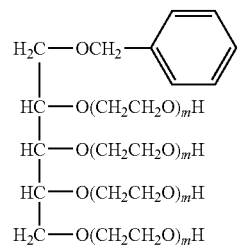

(p1) m=about 245

Example 1-7

A hundred grams (2.5 mmol) of the compound (p1) obtained in the above 1-6 and 320 g of toluene were charged and the whole was heated under reflux to effect azeotropic removal of water. After cooling to room temperature, 1.6 g (16 mmol) of triethylamine and 1.5 g (13 mmol) of methanesulfonyl chloride were added thereto, followed by 6 hours of reaction at 40° C. The reaction liquid was filtered and the filtrate was transferred into a 500 ml round-bottom flask fitted with a thermometer, a nitrogen-introducing tube, a stirrer, and a condenser tube. Then, 19.3 g (100 mmol) of a 28% methanol solution of sodium methoxide was added thereto, followed by 6 hours of reaction at 40° C. Subsequently, 27 g of an adsorbent "KYOWARD 700" (manufactured by Kyowa Chemical Industry Co., Ltd.) was added to the reaction liquid and the whole was further stirred at 70° C. for 1 hour to adsorb excessive sodium methoxide. After filtration of the reaction liquid, the filtrate was charged into a 1 L beaker and crystallization was carried out with adding 300 g of ethyl acetate and 350 g of hexane. The precipitated crystals were collected into a 1 L beaker by filtration and dissolved under heating at 40° C. with adding 400 g of ethyl acetate. Thereafter, crystallization was again carried out with adding 300 g of hexane. The precipitated crystals were collected by filtration and dried to obtain the following compound (p2).

$^1$H-NMR (CDCl$_3$, internal standard TMS) δ (ppm): 3.37 (12H, s, —OCH$_3$), 3.30-3.90 (3623H, m, —CH$_2$O (CH$_2$CH$_2$O)$_m$CH$_3$, CHO(CH$_2$CH$_2$O)$_m$CH$_3$, CH$_2$OCH$_2$Ph), 4.48-4.57 (2H, m, —CH$_2$Ph), 7.27-7.38 (5H, m, —CH$_2$Ph)

GPC analysis; number average molecular weight (Mn): 37215, weight average molecular weight (Mw): 38037, polydispersity (Mw/Mn): 1.03, peak top molecular weight (Mp): 38912

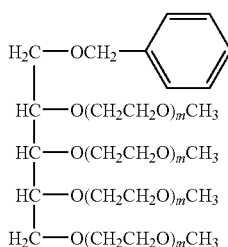

(p2) m=about 245

Example 1-8

Into a 500 ml round-bottom flask fitted with a thermometer, a nitrogen-introducing tube, a stirrer, and a condenser tube were added 15 g of the compound (p2) obtained in the above 1-7 and 15 g of 5% palladium-carbon (50% hydrous product). After the replacement by nitrogen, 300 ml of methanol and 150 ml of cyclohexene were added thereto, temperature was elevated to result in gentle reflux at 52 to 55° C., and reaction was carried out for 5 hours. After cooling of the reaction mixture to room temperature, the palladium-carbon was removed by filtration and the filtrate was concentrated. The concentrate was crystallized with adding 50 ml of ethyl acetate and 50 ml of hexane. The resulting crystals were collected by filtration and dried to obtain the following compound (p3).

$^1$H-NMR (CDCl$_3$, internal standard TMS) δ (ppm): 3.38 (12H, s, CH$_3$—O—), 3.52-3.77 (2H, m, —O—CH$_2$—), 3.45-3.63 (6H, m, —CH$_2$—O—, —CH—O—)

GPC analysis; number average molecular weight (Mn): 36716, weight average molecular weight (Mw): 38876, polydispersity (Mw/Mn): 1.03, peak top molecular weight (Mp): 38876

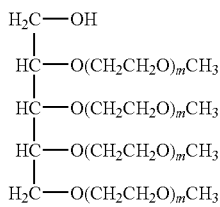

(p3) m=about 245

Example 1-9

Case of Molecular Weight of About 20000

Into a 100 ml beaker containing 47.4 g of methanol and 13.5 g of ion-exchange water was charged 6.8 g of potassium hydroxide, which was dissolved at room temperature. After dissolution, the prepared potassium hydroxide solution and 36.0 g (0.14 mol) of the compound obtained in the above 1-5 were added to a 5 L autoclave and, after stirring at room temperature for 15 minutes, 360 g of toluene was charged thereinto. With introduction of nitrogen thereinto, the whole was treated at 105 to 110° C. to recover 210 g of water, methanol, and toluene and then was cooled to 50° C. or lower. Then, 360 g of anhydrous grade toluene was charged thereinto and, with introduction of nitrogen thereinto at 105 to 110° C., 220 g of water, methanol, and toluene was recovered. The inside of the 5 L autoclave system was replaced by nitrogen and 258 g (5.9 mol) of ethylene oxide was added thereto at 80 to 150° C. under a pressure of 1 MPa or less, followed by continuation of the reaction for another 1 hour. The resulting reaction product was taken out in an amount of 800 g, and 675 g (15.3 mol) of ethylene oxide was added thereto at 80 to 150° C. under a pressure of 1 MPa or less, followed by continuation of the reaction for another 1 hour. After 800 g was removed from the autoclave, pH was adjusted to 7.5 with an 85% aqueous phosphoric acid solution to obtain the following compound (p4).

$^1$H-NMR (CDCl$_3$, internal standard TMS) δ (ppm): 3.40-3.80 (1803H, m, —CH$_2$O(CH$_2$CH$_2$O)$_m$H, CHO(CH$_2$CH$_2$O)$_m$H, CH$_2$OCH$_2$Ph), 4.48-4.57 (2H, m, —CH$_2$Ph), 7.27-7.38 (5H, m, —CH$_2$Ph)

GPC analysis; number average molecular weight (Mn): 15882, weight average molecular weight (Mw): 16523, polydispersity (Mw/Mn): 1.04, peak top molecular weight (Mp): 16945

TOF-MS analysis: 18859

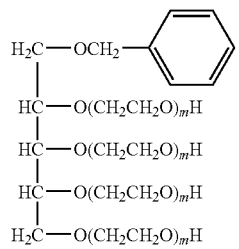

(p4) m=about 106

Example 1-10

Into a 1000 L round-bottom flask fitted with a thermometer, a nitrogen-introducing tube, a stirrer, a Dean-stark tube, and a condenser tube were charged 200 g (10 mmol) of the compound (p4) obtained in the above 1-9 and 700 g of toluene and the whole was heated under reflux to effect azeotropic removal of water. After cooling to room temperature, 7.01 g (69 mmol) of triethylamine and 6.45 g (56 mmol) of methanesulfonyl chloride were added thereto, followed by 3 hours of reaction at 40° C. Then, 25.1 g (130 mmol) of a 28% methanol solution of sodium methoxide was added thereto, followed by 3 hours of reaction at 40° C. After the reaction, methanol was removed by evaporation at 40° C. under reduced pressure and, after the residue was diluted with 2000 g of toluene, the solution was filtrated. Then, 1000 g of a 25% aqueous sodium chloride solution was added to the filtrate and the whole was stirred at 50° C., followed by washing with water twice. After magnesium sulfate was added to toluene in an appropriate amount to remove water and filtration was conducted, crystallization was carried out with adding hexane until crystals were precipitated. After the precipitated crystals were collected by filtration and again dissolved under heating at 40° C. with adding ethyl acetate, crystallization was again carried out with adding hexane until crystals were precipitated. The precipitated crystals were collected by filtration and dried to obtain the following compound (p5).

$^1$H-NMR (CDCl$_3$, internal standard TMS) δ (ppm): 3.40-3.80 (1799H, m, —CH$_2$O(CH$_2$CH$_2$O)$_m$H, CHO(CH$_2$CH$_2$O)$_m$H, CH$_2$OCH$_2$Ph), 4.48-4.57 (2H, m, —CH$_2$Ph), 7.27-7.38 (5H, m, —CH$_2$Ph)

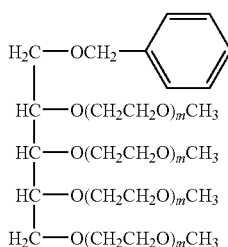

(p5) m=about 106

Example 1-11

Into a 500 ml round-bottom flask fitted with a thermometer, a nitrogen-introducing tube, a stirrer, and a condenser tube were charged 170 g of the compound (p5) obtained in the above 1-10 and 85 g of 5% palladium-carbon (50% hydrous product). After the replacement by nitrogen, 1700 ml of methanol and 284 ml of cyclohexene were added thereto, temperature was elevated to result in gentle reflux at 52 to 55° C., and reaction was carried out for 3 hours. After cooling of the reaction mixture to room temperature, the palladium-carbon was removed by filtration and the filtrate was concentrated. The concentrate was crystallized with adding ethyl acetate and hexane. The resulting crystals were collected by filtration and dried to obtain the following compound (p6).

$^1$H-NMR (CDCl$_3$, internal standard TMS) δ (ppm): 3.38 (12H, s, CH$_3$—O—), 3.40-3.80 (1800H, m, —CH$_2$O(CH$_2$CH$_2$O)$_m$H, CHO(CH$_2$CH$_2$O)$_m$H, CH$_2$OCH$_2$Ph)

GPC analysis; number average molecular weight (Mn): 15184, weight average molecular weight (Mw): 15762, polydispersity (Mw/Mn): 1.038, peak top molecular weight (Mp): 16112

TOF-MS analysis: 18859

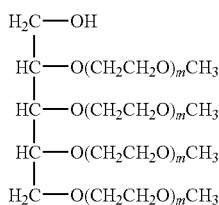

(p6) m=about 106

Example 1-12

Case of Molecular Weight of 60000

To about 550 g of the reaction liquid remaining in the reaction autoclave in Example 1-9 was added 1700 g of toluene. After 400 g of toluene was removed by evaporation at 110° C., 526 g (12.0 mol) of ethylene oxide was added thereto at 80 to 150° C. under a pressure of 1 MPa or less, followed by continuation of the reaction for another 1 hour. The resulting reaction product was taken out in an amount of 800 g, and 215 g (4.9 mol) of ethylene oxide was added thereto at 80 to 150° C. under a pressure of 1 MPa or less, followed by continuation of the reaction for another 1 hour. After 700 g was removed from the autoclave, pH was adjusted to 7.5 with an 85% aqueous phosphoric acid solution and toluene was removed by evaporation to obtain the following compound (p7).

$^1$H-NMR (CDCl$_3$, internal standard TMS) δ (ppm): 3.40-3.80 (3623H, m, —CH$_2$O(CH$_2$CH$_2$O)$_m$H, CHO(CH$_2$CH$_2$O)$_m$H, CH$_2$OCH$_2$Ph), 4.48-4.57 (2H, m, —CH$_2$Ph), 7.27-7.38 (5H, m, —CH$_2$Ph)

GPC analysis; number average molecular weight (Mn): 51374, weight average molecular weight (Mw): 52903, polydispersity (Mw/Mn): 1.03, peak top molecular weight (Mp): 53220

TOF-MS analysis: 58852

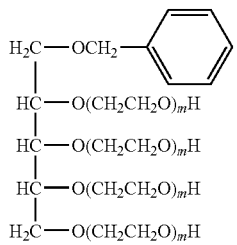

(p7) m=about 333

Example 1-13

Into a 2000 L round-bottom flask fitted with a thermometer, a nitrogen-introducing tube, a stirrer, a Dean-stark tube, and a condenser tube were charged 104 g (1.7 mmol) of the compound (p7) obtained in the above 1-12 and 364 g of toluene and the whole was heated under reflux to effect azeotropic removal of water. After cooling to room temperature, 1.30 g (13 mmol) of triethylamine and 1.19 g (10 mmol) of methanesulfonyl chloride were added thereto, followed by 3 hours of reaction at 40° C. Then, 4.65 g (24 mmol) of a 28% methanol solution of sodium methoxide was added thereto, followed by 12 hours of reaction at 40° C. After the reaction, dilution with 728 g of toluene was conducted and then methanol was removed by evaporation under reduced pressure, followed by filtration. Then, 520 g of a 25% aqueous sodium chloride solution was added to the filtrate and the whole was stirred at 50° C., followed by washing with water twice. After magnesium sulfate was added to toluene in an appropriate amount to remove water and filtration was conducted, crystallization was carried out with adding hexane until crystals were precipitated. After the precipitated crystals were collected by filtration and again dissolved under heating at 40° C. with adding ethyl acetate, crystallization was again carried out with adding hexane until crystals were precipitated. The precipitated crystals were collected by filtration and dried to obtain the following compound (p8).

$^1$H-NMR (CDCl$_3$, internal standard TMS) δ (ppm): 3.37 (12H, s, —OCH$_3$), 3.30-3.90 (5447H, m, —CH$_2$O(CH$_2$CH$_2$O)$_m$CH$_3$, CHO(CH$_2$CH$_2$O)$_m$CH$_3$, CH$_2$OCH$_2$Ph), 4.48-4.57 (2H, m, —CH$_2$Ph), 7.27-7.38 (5H, m, —CH$_2$Ph)

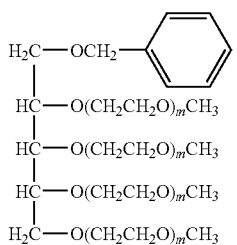

(p8) m=about 333

Example 1-14

Case of Molecular Weight of 80000

To about 800 g of the reaction liquid remaining in the reaction autoclave in Example 1-12 was added 165 g (3.75 mol) of ethylene oxide at 80 to 150° C. under a pressure of 1 MPa or less, followed by continuation of the reaction for another 1 hour. Then, pH was adjusted to 7.5 with an 85% aqueous phosphoric acid solution and toluene was removed by evaporation to obtain the following compound (p9).

$^1$H-NMR (CDCl$_3$, internal standard TMS) δ (ppm): 3.40-3.80 (7255H, m, —CH$_2$O(CH$_2$CH$_2$O)$_m$H, CHO(CH$_2$CH$_2$O)$_m$H, CH$_2$OCH$_2$Ph), 4.48-4.57 (2H, m, —CH$_2$Ph), 7.27-7.38 (5H, m, —CH$_2$Ph)

GPC analysis; number average molecular weight (Mn): 67291, weight average molecular weight (Mw): 68988, polydispersity (Mw/Mn): 1.03, peak top molecular weight (Mp): 70163

TOF-MS analysis: 78138

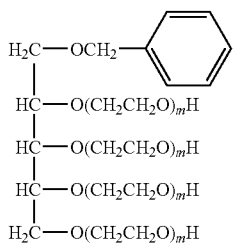

(p9) m=about 443

Example 2-1

Synthesis of activated ester body (p10) (case of R$^1$=methyl group, OA$^1$, OA$^2$=oxyethylene group, n=0, and molecular weight of about 40000)

Into a 100 ml round-bottom flask fitted with a thermometer, a nitrogen-introducing tube, a stirrer, and a condenser tube were added 2 g of the compound (p3) obtained in the above Example 1-8 and 18 g of toluene, and the whole was heated to 40° C. to dissolve them. After dissolution, the mixture was heated to 110° C. to remove water and, after cooling to 40° C., 0.12 g of N,N'-disuccinimidyl carbonate and 0.055 g of pyridine were added thereto, followed by 4 hours of reaction at 80° C. After 4 hours, the reaction liquid was filtrated and hexane was added to the filtrate until crystals were precipitated. After the crystals were collected by filtration and dissolved into ethyl acetate under heating, hexane was added until crystals were precipitated and the crystals were collected by filtration and dried to obtain the objective compound (p10).

$^1$H-NMR (CDCl$_3$, internal standard TMS) δ (ppm): 2.84 (4H, Br, —C(O)CH$_2$CH$_2$C(O)—), 3.38 (12H, s, —CH$_3$), 3.40-4.00 (3621H, m, —CH$_2$O(CH$_2$CH$_2$O)$_m$CH$_3$, CHO (CH$_2$CH$_2$O)$_m$CH$_3$, CH$_2$OCH$_2$CN), 4.55-4.58 (1H, m, —OC(O)OCH$_2$CH—), 4.58-4.64 (1H, m, —OC(O)OCH$_2$CH—)

GPC analysis; number average molecular weight (Mn): 35662, weight average molecular weight (Mw): 36816, polydispersity (Mw/Mn): 1.03, peak top molecular weight (Mp): 37789

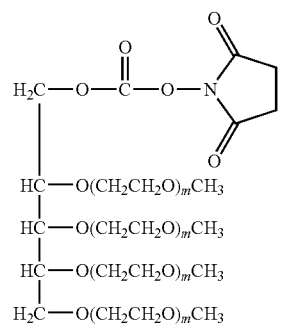

(p10) m=about 245

Example 2-2

Synthesis of activated ester body (p11) (case of R$^1$=methyl group, OA$^1$, OA$^2$=oxyethylene group, n=0, and molecular weight of about 20000)

Into a 100 ml round-bottom flask fitted with a thermometer, a nitrogen-introducing tube, a stirrer, and a condenser tube were added 10 g of the compound (p6) obtained in the above Example 1-11 and 110 g of toluene, and the whole was heated to 40° C. to dissolve them. After dissolution, the mixture was heated to 110° C. to remove water and, after cooling to 40° C., 1.35 g of N,N'-disuccinimidyl carbonate and 0.624 g of pyridine were added thereto, followed by 4 hours of reaction at 80° C. After 4 hours, the reaction liquid was filtrated and hexane was added to the filtrate until crystals were precipitated. After the crystals were collected by filtration and dissolved into ethyl acetate under heating, hexane was added until crystals were precipitated and the crystals were collected by filtration and dried to obtain the objective compound (p11).

$^1$H-NMR (CDCl$_3$, internal standard TMS) δ (ppm): 2.84 (4H, Br, —C(O)CH$_2$CH$_2$C(O)—), 3.38 (12H, s, —CH$_3$), 3.40-4.00 (1797H, m, —CH$_2$O(CH$_2$CH$_2$O)$_m$CH$_3$, CHO (CH$_2$CH$_2$O)$_m$CH$_3$, CH$_2$OCH$_2$CN), 4.55-4.58 (1H, m, —OC(O)OCH$_2$CH—), 4.58-4.64 (1H, m, —OC(O)OCH$_2$CH—)

GPC analysis; number average molecular weight (Mn): 15153, weight average molecular weight (Mw): 15704, polydispersity (Mw/Mn): 1.04, peak top molecular weight (Mp): 16101

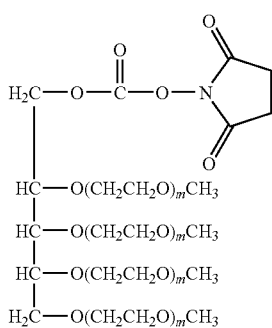

(p11) m=about 106

Example 3-1

Synthesis of p-nitrophenyl carbonate body (b) (case of $R^1$=methyl group, $OA^1$, $OA^2$=oxyethylene group, n=0, and molecular weight of about 40000)

Into a 200 ml round-bottom flask fitted with a thermometer, a nitrogen-introducing tube, a stirrer, a Dean-stark tube, and a condenser tube were charged 20 g (0.5 mmol) of the compound (p3) obtained in the above Example 1-8 and 100 ml of toluene, and the whole was heated under reflux to effect azeotropic removal of water. After cooling of the reaction liquid to 80° C., 0.48 g (4.7 mmol) of triethylamine and 0.76 g (3.7 mmol) of p-nitrophenyl chloroformate were added thereto, followed by 5 hours of reaction at 80° C. After the reaction, the reaction liquid is filtrated and, after 100 ml of ethyl acetate was added to the filtrate, crystals were precipitated with adding 200 ml of hexane. After the precipitated crystals were collected by filtration, 100 ml of ethyl acetate was added to the crystals, and the crystals were dissolved under heating, crystallization was again carried out with adding 100 ml of hexane. The crystallization operation was repeated 5 times in total. The crystals collected by filtration were dried to obtain the following p-nitrophenyl carbonate body (p12).

$^1$H-NMR (CDCl$_3$, internal standard TMS) δ (ppm): 3.38 (6H, s, —CH$_3$), 3.40-3.80 (3616H, m, —CH$_2$O(CH$_2$CH$_2$O)$_m$CH$_3$, CHO(CH$_2$CH$_2$O)$_m$CH$_3$), 4.30-4.50 (2H, m, —CH$_2$OCOOPhNO$_2$), 7.39 (2H, d, -PhNO$_2$), 8.28 (2H, d, -PhNO$_2$)

GPC analysis; number average molecular weight (Mn): 36423, weight average molecular weight (Mw): 37507, polydispersity (Mw/Mn): 1.030, peak top molecular weight (Mp): 38533

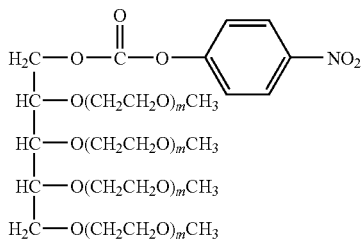

(p12) m=about 245

Example 3-2

Synthesis of p-nitrophenyl carbonate body (b) (case of $R^1$=methyl group, $OA^1$, $OA^2$=oxyethylene group, n=0, and molecular weight of about 20000)

Into a 500 ml round-bottom flask fitted with a thermometer, a nitrogen-introducing tube, a stirrer, a Dean-stark tube, and a condenser tube were charged 50 g (2.5 mmol) of the compound (p6) obtained in the above Example 1-11 and 250 ml of toluene, and the whole was heated under reflux to effect azeotropic removal of water. After cooling of the reaction liquid to 80° C., 2.66 g (26.3 mmol) of triethylamine and 4.24 g (21.0 mmol) of p-nitrophenyl chloroformate were added thereto, followed by 5 hours of reaction at 80° C. After the reaction, the reaction liquid is filtrated and, after ethyl acetate was added to the filtrate, hexane was added until crystals were precipitated. After the precipitated crystals were collected by filtration, ethyl acetate was added to the crystals, and the crystals were dissolved under heating, crystallization was again carried out with adding hexane. The crystallization operation was repeated 5 times in total. The crystals collected by filtration were dried to obtain the following p-nitrophenyl carbonate body (p13).

$^1$H-NMR (CDCl$_3$, internal standard TMS) δ (ppm): 3.38 (12H, s, —CH$_3$), 3.40-3.90 (1797H, m, —CH$_2$O (CH$_2$CH$_2$O)$_m$CH$_3$, CHO(CH$_2$CH$_2$O)$_m$CH$_3$), 4.35-4.60 (2H, m, —CH$_2$OCOOPhNO$_2$), 7.43 (2H, d, -PhNO$_2$), 8.38 (2H, d, -PhNO$_2$)

GPC analysis; number average molecular weight (Mn): 15297, weight average molecular weight (Mw): 15839, polydispersity (Mw/Mn): 1.035, peak top molecular weight (Mp): 16226

TOF-MS: 19140

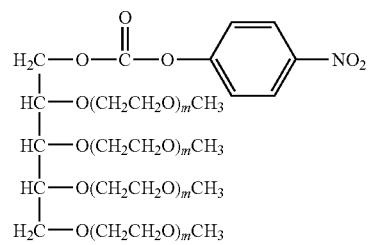

(p13) m=about 106

Example 4-1

Synthesis of nitrile body (p14) (case of $R^1$=methyl group, $OA^1$, $OA^2$=oxyethylene group, n=0, and molecular weight of about 40000)

Into a 500 ml round-bottom flask fitted with a thermometer, a nitrogen-introducing tube, a stirrer, and a condenser tube were added 70 g of the compound (p3) obtained in the above Example 1-8 and 70 ml of ion-exchange water, and the whole was heated to 40° C. to dissolve them. After dissolution, the whole was cooled to 10° C. or lower and 4.38 g of a 50% aqueous potassium hydroxide solution was added thereto. Subsequently, 210 g of acrylonitrile was added dropwise over a period of 2 hours while the whole was kept at 5 to 10° C. After completion of the dropwise addition, the reaction was carried out for another 2 hours and 26.25 g of an 8.5% aqueous phosphoric acid solution was added dropwise to effect neutralization.

After 140 g of ion-exchange water was added to the reaction liquid, the mixture was transferred to a separating funnel and 210 ml of ethyl acetate was added, followed by stirring. Thereafter, the mixture was allowed to stand and the upper ethyl acetate layer was discarded. The extraction with ethyl acetate was repeated six times. After completion of the extraction, extraction was conducted with 280 ml of chloroform. The resulting chloroform layer was dried over magnesium sulfate and, after filtration, was concentrated. The concentrate was dissolved with adding 700 ml of ethyl acetate thereto and hexane was added until crystals were precipitated. The crystals were collected by filtration and again dissolved into 700 ml of ethyl acetate under heating. After cooling to room temperature, hexane was added until crystals were precipitated. The crystals was collected by filtration and dried to obtain the following nitrile body (p14).

$^1$H-NMR (CDCl$_3$, internal standard TMS) δ (ppm): 2.59-2.66 (2H, m, —CH$_2$CH$_2$CN), 3.38 (12H, s, —CH$_3$), 3.40-3.80 (3625H, m, —CH$_2$O(CH$_2$CH$_2$O)$_m$CH$_3$, CHO(CH$_2$CH$_2$O)$_m$CH$_3$, CH$_2$OCH$_2$CH$_2$CN)

GPC analysis; number average molecular weight (Mn): 36372, weight average molecular weight (Mw): 37433, polydispersity (Mw/Mn): 1.029, peak top molecular weight (Mp): 38503

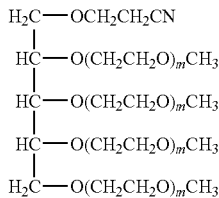

(p14) m=about 245

Example 4-2

Synthesis of nitrile body (p15) (case of R$^1$=methyl group, OA$^1$, OA$^2$=oxyethylene group, n =0, and molecular weight of about 20000)

Into a 500 ml round-bottom flask fitted with a thermometer, a nitrogen-introducing tube, a stirrer, and a condenser tube were added 40 g of the compound (p6) obtained in the above Example 1-11 and 40 g of ion-exchange water, and the whole was heated to 40° C. to dissolve them. After dissolution, the whole was cooled to 10° C. or lower and 2.5 g of a 50% aqueous potassium hydroxide solution was added thereto. Subsequently, 111 g of acrylonitrile was added dropwise over a period of 2 hours while the whole was kept at 5 to 10° C. After completion of the dropwise addition, the reaction was carried out for another 2 hours and 15 g of an 8.5% aqueous phosphoric acid solution was added dropwise to effect neutralization.

After 80 g of ion-exchange water was added to the reaction liquid, the mixture was transferred to a separating funnel and ethyl acetate was added, followed by stirring. Thereafter, the mixture was allowed to stand and the upper ethyl acetate layer was discarded. The extraction with ethyl acetate was repeated six times. After completion of the extraction, extraction was conducted with chloroform. After the resulting chloroform layer was concentrated, the concentrate was dissolved into ethyl acetate and dried over magnesium sulfate. After filtration, hexane was added until crystals were precipitated. The crystals were collected by filtration and again dissolved into ethyl acetate under heating. After cooling to room temperature, hexane was added until crystals were precipitated. The crystals was collected by filtration and dried to obtain the following nitrile body (p15).

$^1$H-NMR (CDCl$_3$, internal standard TMS) δ (ppm): 2.59-2.66 (2H, m, —CH$_2$CH$_2$CN), 3.38 (12H, s, —CH$_3$), 3.40-3.80 (1801H, m, —CH$_2$O(CH$_2$CH$_2$O)$_m$CH$_3$, CHO(CH$_2$CH$_2$O)$_m$CH$_3$, CH$_2$OCH$_2$CH$_2$CN)

GPC analysis; number average molecular weight (Mn): 15268, weight average molecular weight (Mw): 15799, polydispersity (Mw/Mn): 1.03, peak top molecular weight (Mp): 16203

TOF-MS: 18968

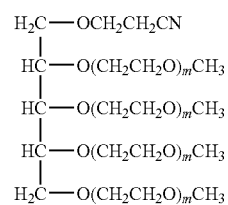

(p15) m=about 106

Example 5-1

Synthesis of amino body (case of R$^1$=methyl group, OA$^1$, OA$^2$=oxyethylene group, n=0, and molecular weight of about 40000)

Into a 1 L autoclave were added 50 g of the nitrile body of the compound (p14) obtained in the above Example 4-1, 500 g of toluene, and 4.5 g of nickel (5136p manufactured by N E M Cat Company) and temperature was elevated to 60° C. Pressure was increased with ammonia until inner pressure reached 0.7 MPa and then increased with hydrogen until inner pressure reached 4.5 MPa, followed by 3 hours of reaction at 130° C. After the reaction, the reaction liquid was cooled to 70° C. and purging with nitrogen was repeated until ammonia odor disappeared. The whole amount of the reaction liquid was taken out and filtrated and the filtrate was cooled to room temperature. Thereafter, hexane was added until crystals were precipitated. The crystals were collected by filtration and dried to obtain the following amine body (p16).

$^1$H-NMR (DSS, internal standard TMS) δ (ppm): 1.82-1.90 (2H, m, —CH$_2$CH$_2$CH$_2$NH$_2$), 2.90-2.97 (2H, m, —CH$_2$CH$_2$CH$_2$NH$_2$), 3.38 (6H, s, —CH$_3$), 3.40-3.80 (4047H, m, —CH$_2$O(CH$_2$CH$_2$O)$_m$CH$_3$, CHO(CH$_2$CH$_2$O)$_m$CH$_3$, CH$_2$OCH$_2$CH$_2$CH$_2$NH$_2$)

GPC analysis; number average molecular weight (Mn): 35978, weight average molecular weight (Mw): 36959, polydispersity (Mw/Mn): 1.027, peak top molecular weight (Mp): 37639

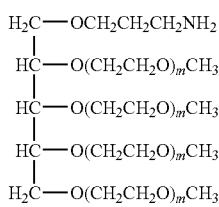

(p16) m=about 245

Example 5-2

Synthesis of amino body (case of $R^1$=methyl group, $OA^1$, $OA^2$=oxyethylene group, n=0, and molecular weight of about 20000)

Into a 1 L autoclave were added 20 g of the nitrile body of the formula (p15) obtained in Example 4-2, 500 g of toluene, and 1.2 g of nickel (5136p manufactured by N E M Cat Company) and temperature was elevated to 60° C. Pressure was increased with ammonia until inner pressure reached 0.7 MPa and then increased with hydrogen until inner pressure reached 4.5 MPa, followed by 3 hours of reaction at 130° C. After the reaction, the reaction liquid was cooled to 70° C. and purging with nitrogen was repeated until ammonia odor disappeared. The whole amount of the reaction liquid was taken out and filtrated and the filtrate was cooled to room temperature. Thereafter, hexane was added until crystals were precipitated. The crystals were collected by filtration and dried to obtain the following amine body (p17).

$^1$H-NMR (D$_2$O, internal standard DSS) δ (ppm): 1.82 (2H, m, —CH$_2$CH$_2$CH$_2$NH$_2$), 2.90-2.97 (2H, m, —CH$_2$CH$_2$CH$_2$NH$_2$), 3.38 (6H, s, —CH$_3$), 3.40-3.80 (1801H, m, —CH$_2$O(CH$_2$CH$_2$O)$_m$CH$_3$, CHO(CH$_2$CH$_2$O)$_m$CH$_3$, CH$_2$OCH$_2$CH$_2$CH$_2$NH$_2$)

GPC analysis; number average molecular weight (Mn): 35978, weight average molecular weight (Mw): 36959, polydispersity (Mw/Mn): 1.027, peak top molecular weight (Mp): 37639

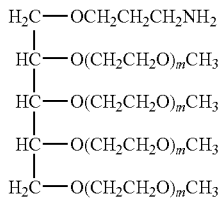

(p17) m=about 106

Example 6

Synthesis of terminal acetal body (p18) (case of $R^1$=methyl group, $OA^1$, $OA^2$=oxyethylene group, n=0, and molecular weight of about 20000)

Into a 100 ml round-bottom flask fitted with a thermometer, a nitrogen-introducing tube, a stirrer, and a condenser tube were added 20 g of the compound (p13) obtained in the above Example 3-2 and 80 g of toluene, and the whole was heated to 40° C. to dissolve them. After dissolution, 0.47g of 1-amino-3,3-diethoxypropane was added and the whole was reacted at 50° C. for 2 hours. After the reaction, KYOWARD #2000 and KYOWARD #700 (manufactured by Kyowa Chemical Industry Co., Ltd.) were added to the solution diluted with 80 g of toluene and stirring was conducted at 60° C. for 30 minutes, followed by filtration. Hexane was added to the filtrate until crystals were precipitated. The precipitated crystals were collected by filtration and 200 g of ethyl acetate was added to the crystals. After 200 g of ethyl acetate was added to the crystals and the crystals were dissolved under heating, crystallization was again carried out with adding 120 g of hexane. The crystals collected by filtration were dried to obtain the following 3,3-diethoxypropyl carbamate body (p18).

$^1$H-NMR (CDCl$_3$, internal standard TMS) δ (ppm): 1.26 (6H, t, —CH(OCH$_2$CH$_3$)$_2$), 1.34 (2H, dt, —NHCH$_2$CH$_2$CH(OCH$_2$CH$_3$)$_2$), 3.30 (2H, dt, —NHCH$_2$CH$_2$CH(OCH$_2$CH$_3$)$_2$), 3.38 (12H, s, —CH$_3$), 3.40-3.99 (1803H, m, —CH$_2$O(CH$_2$CH$_2$O)$_m$CH$_3$, CHO(CH$_2$CH$_2$O)$_m$CH$_3$, CH$_2$OCH$_2$CH$_2$), 4.13-4.32 (2H, m, —CH2OCONHCH2-), 4.55 (1H, t, —NHCH$_2$CH$_2$CH(OCH$_2$CH$_3$)$_2$), 5.32 (1H, m, —NHCH$_2$CH$_2$CH(OCH$_2$CH$_3$)$_2$)

TOF-MS analysis: 19170

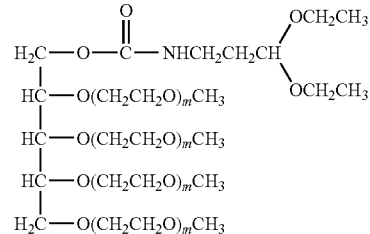

(p18) m=about 106

Example 7

Synthesis of aldehyde body (p19) (case of $R^1$=methyl group, $OA^1$, $OA^2$=oxyethylene group, n =0, and molecular weight of about 20000)

Into a 1000 ml round-bottom flask fitted with a thermometer, a nitrogen-introducing tube, a stirrer, and a condenser tube were added 16 g of the compound (p18) obtained in the above Example 6 and 800 g of pure water, and pH was adjusted with a phosphoric acid solution to 2, followed by reaction at room temperature. After 3 hours, sodium chloride was added and pH was adjusted with sodium hydroxide to 7, followed by extraction with chloroform. After concentration, the extract was dissolved into ethyl acetate, and water was removed with a drying agent. After filtration, hexane was added to the filtrate until crystals were precipitated, thereby obtaining the following aldehyde body (p19).

$^1$H-NMR (CDCl$_3$, internal standard TMS) δ (ppm): 2.72 (2H, t, —NHCH$_2$CH$_2$CHO), 3.38 (12H, s, —CH$_3$), 3.46 (2H, dt, —NHCH$_2$CH$_2$CHO), 3.40-4.00 (1797H, m, —CH$_2$O(CH$_2$CH$_2$O)$_m$CH$_3$, CHO(CH$_2$CH$_2$O)$_m$CH$_3$, CH$_2$OCH$_2$CH$_2$CN), 4.13-4.31 (2H, m, —CH$_2$OCONHCH$_2$—), 5.44 (1H, m, —NHCH$_2$CH$_2$CH(OCH$_2$CH$_3$)$_2$), 9.80 (1H, s, —CHO)

TOF-MS analysis: 19103

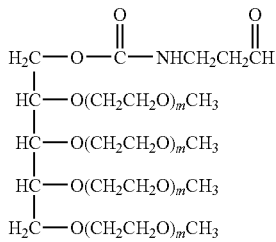

(p19) m=about 106

Example 8

Synthesis of maleimide body (p20) (case of R$^1$=methyl group, OA$^1$, OA$^2$=oxyethylene group, n=0, and molecular weight of about 20000)

Into a 200 ml round-bottom flask fitted with a thermometer, a nitrogen-introducing tube, a stirrer, and a condenser tube were added 15 g (0.75 mmol) of the compound (p17) obtained in the above Example 5-2, 78 g of toluene, and 12 g of acetonitrile. After dissolution, 0.38 (3.65 mmol) of N-methylmorpholine was added at room temperature and 0.299 g (1.12 mmol) of 3-maleimidopropionic acid N-succinimidyl ester is added, followed by reaction at room temperature. Four hours later, after filtration was carried out, the filtrate was diluted with ethyl acetate and hexane was added until crystals were precipitated. After filtration, the crystals were collected and then dissolved into ethyl acetate and hexane was added until crystals were precipitated. After filtration, the crystals were dried to obtain the following maleimide body (p20).

$^1$H-NMR (CDCl$_3$, internal standard TMS) δ (ppm): 1.71-1.76 (2H, m, —OCH$_2$CH$_2$CH$_2$NH—), 2.47-2.50 (2H, t, —NHCOCH$_2$CH$_2$N), 3.38 (12H, s, —CH$_3$), 3.40-4.00 (1808H, m, —CH$_2$O(CH$_2$CH$_2$O)$_m$CH$_3$, CHO(CH$_2$CH$_2$O)$_m$CH$_3$, CH$_2$OCH$_2$CH$_2$), 6.59 (1H, Br, —CH$_2$NHCOCH$_2$CH$_2$N—), 6.71 (2H, s, —CH═CH—)

GPC analysis; number average molecular weight (Mn): 15348, weight average molecular weight (Mw): 16006, polydispersity (Mw/Mn): 1.043, peak top molecular weight (Mp): 16091

TOF-MS analysis: 19015

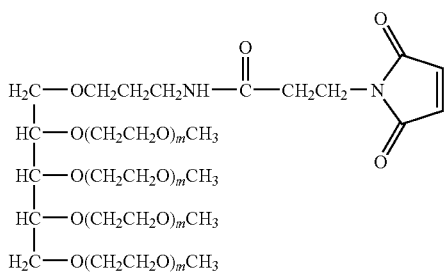

(p20) m=about 106

Example 9

Synthesis of acetylene body (p21) (case of R$^1$=methyl group, OA$^1$=oxyethylene group, n=0, and molecular weight of about 40000)

Into a 1000 ml round-bottom flask fitted with a thermometer, a nitrogen-introducing tube, a stirrer, and a condenser tube were added 2 g of the compound (p12) obtained in the above Example 3-1 and 16 g of toluene. After dissolution at 50° C., propargylamine was added and reaction was carried out at 50° C. After 4 hours, the mixture was diluted with toluene and KYOWARD #2000 and KYOWARD #700 were added. After 30 minutes of stirring at 50° C., KYOWARD was removed by filtration and the same operation was again carried out. Hexane was added to the filtrate until crystals were precipitated and, after filtration, the crystals were dissolved into ethyl acetate. Hexane was added until crystals were precipitated and, after filtration, the crystals were dried to obtain the following acetylene body (p21).

$^1$H-NMR(CDCl$_3$, internal standard TMS) δ (ppm): 1.99 (1H, s, —NHCH$_2$CCH), 3.38 (12H, s, —CH$_3$), 3.40-4.00 (3623H, m, —CHCH$_2$O—, (CH$_2$CH$_2$O), CHO(CH$_2$CH$_2$O)$_m$CH$_3$, CH$_2$), 4.14-4.36 (2H, m, —CH$_2$OCONHCH$_2$CCH), 5.63 (1H, br, —OCONHCH)

GPC analysis; number average molecular weight (Mn): 35954, weight average molecular weight (Mw): 37895, polydispersity (Mw/Mn): 1.054, peak top molecular weight (Mp): 37132

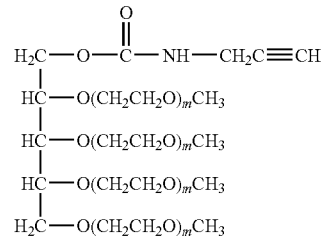

(p21) m=about 245

Example 10

Synthesis of (p22) (case of R$^1$=methyl group, OA$^1$, OA$^2$=oxyethylene group, n≥1, and molecular weight of about 50000)

Into a 1000 ml round-bottom flask fitted with a thermometer, a nitrogen-introducing tube, a stirrer, and a condenser tube were added 2 g of the compound (p12) obtained in the above Example 3-1 and 8 g of toluene. Then, α-aminopropyl-ω-hydroxypolyoxyethylene (molecular weight of about 10000) was added and reaction was carried out at 50° C. After 2 hours, the mixture was diluted with toluene and KYOWARD #2000 and KYOWARD #700 were added. After 30 minutes of stirring at 50° C., KYOWARD was removed by filtration and the same operation was again carried out. Hexane was added to the filtrate until crystals were precipitated to obtain the following alcohol body (p22).

$^1$H-NMR (CDCl$_3$, internal standard TMS) δ (ppm): 1.75 (2H, m, —NHCH$_2$CH$_2$CH$_2$O—), 3.38 (12H, s, —CH$_3$), 3.40-4.00 (4532H, m, —(CH$_2$CH$_2$O), —C(O)H, —OCH$_2$—, NHCH$_2$CH$_2$CH$_2$), 5.20 (1H, br, —CH$_2$OCONHCH$_2$CH$_2$CH$_2$O—)

GPC analysis; number average molecular weight (Mn): 42473, weight average molecular weight (Mw): 43608, polydispersity (Mw/Mn): 1.03, peak top molecular weight (Mp): 43530

TOF-MS analysis: 53473

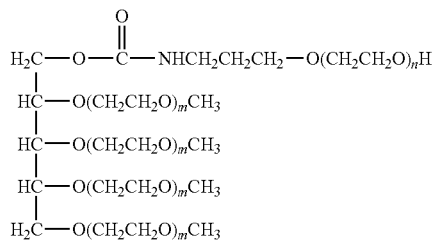

(p22). m=about 245 n=about 226

Example 11

Synthesis of p-nitrophenyl carbonate body (p23) (case of $R^1$=methyl group, $OA^1$, $OA^2$=oxyethylene group, n≥1, and molecular weight of about 50000)

Into a 500 ml round-bottom flask fitted with a thermometer, a nitrogen-introducing tube, a stirrer, a Dean-Stark tube, and a condenser tube were added 1 g 2.5 mmol) of the compound (p22) obtained in the above Example 10 and 10 g of anhydrous toluene. After dissolution under heating at 40 to 80° C., triethylamine and p-nitrophenyl chloroformate were added, followed by 5 hours of reaction at 80° C. After completion of the reaction, the reaction liquid was filtrated and, after 400 g of ethyl acetate was added to the filtrate, 200 g of hexane was added thereto to precipitate crystals. After the precipitated crystals were collected by filtration, 500 ml of ethyl acetate was added to the crystals, and the crystals were dissolved under heating, crystallization was again carried out with adding 200 ml of hexane. The crystals collected by filtration were dried to obtain the following p-nitrophenyl carbonate body (p24).

$^1$H-NMR (CDCl$_3$, internal standard TMS) δ (ppm): 1.76-1.80 (2H, m, —NHCH$_2$CH$_2$CH$_2$O—), 3.38 (12H, s, —CH$_3$), 3.40-4.00 (4529H, m, —(CH$_2$CH$_2$O), —C(O)H, —OCH$_2$—, NHCH$_2$CH$_2$CH$_2$), 4.43-4.53 (2H, m, —OCH$_2$CH$_2$OCOCPh), 5.24 (1H, br, —CONHCH$_2$), 7.40 (2H, d, OCOPhNO$_2$), 8.29 (2H, d, OCOPhNO$_2$)

GPC analysis; number average molecular weight (Mn): 41653, weight average molecular weight (Mw): 43322, polydispersity (Mw/Mn): 1.04, peak top molecular weight (Mp): 42425

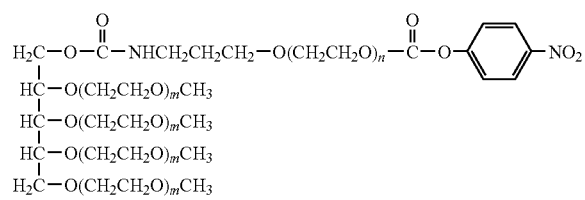

(p24) m=245 n=226
(Data)

Using ion-exchange water, a 10% aqueous solution of a polyoxyalkylene compound was prepared and viscosity was measured. Viscometer: E-type viscometer RE105L manufactured by Toki Sangyo Co., Ltd.
Condition: temperature 40° C.

TABLE 1

Viscosity of Polyoxyalkylene Compound Having Molecular Weight of 40,000 in 10% Aqueous Solution

| Compound No. | Molecular weight | Alkylene oxide (AO species) | Number of branches | Viscosity (η) mPa·s |
|---|---|---|---|---|
| CH$_3$—(OA)$_n$—OH | 40,000 | EO | 1 | 19.3 |
| (26) | 40,000 | EO | 2 | 18.8 |
| (27) | 40,000 | EO | 2 + 4 | 10.9 |
| (p3) | 40,000 | EO | 4 | 9.6 |

EO: ethylene oxide

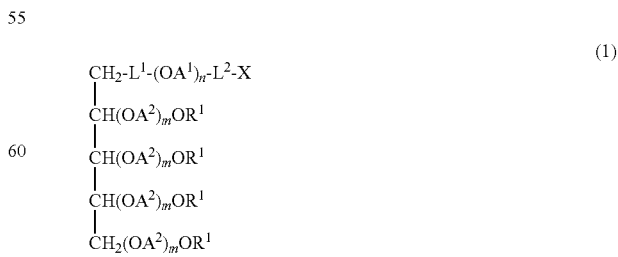

The multibranched polyoxyalkylene compound obtained by the invention improves viscosity and, in the case where the compound modifies bio-related substances and is utilized in pharmaceutical applications including aqueous solution preparations such as an injection preparation, it is considered that influence of the viscosity by the polyoxyalkylene compound is improved.

While the invention has been described in detail and with reference to specific embodiments thereof, it will be apparent to one skilled in the art that various changes and modifications can be made therein without departing from the spirit and scope thereof.

Incidentally, the present application is based on Japanese Patent Application No. 2009-088461 filed on Mar. 31, 2009, and the contents are incorporated herein by reference. Also, all the references cited herein are incorporated as a whole.

The invention claimed is:

1. A multibranched polyoxyalkylene compound represented by the following formula (1):

$$CH_2\text{-}L^1\text{-}(OA^1)_n\text{-}L^2\text{-}X \\ | \\ CH(OA^2)_m OR^1 \\ | \\ CH(OA^2)_m OR^1 \\ | \\ CH(OA^2)_m OR^1 \\ | \\ CH_2(OA^2)_m OR^1$$ (1)

wherein $R^1$ is the same or different and is a hydrocarbon group having 1 to 24 carbon atoms, $OA^1$ and $OA^2$ are the same or different and are an oxyalkylene group having 2 to 4 carbon atoms, n and m are the same or different and are an average number of moles of the oxyalkylene group added, n represents 0 to 1000, m is the same or different and represents 10 to 1000, X represents a functional group capable of reacting with an amino group, a mercapto group, an aldehyde group, a carboxyl group, a triple bond, or an azide group to form a chemical bond, and $L^1$ and $L^2$ are the same or different and are a single bond, an alkylene group, or an alkylene group in which at least one bond selected from an ester bond, a urethane bond, an amide bond, an ether bond, a carbonate bond, and an amino is interposed.

2. The multibranched polyoxyalkylene compound according to claim 1, wherein $R^1$ is the same or different and is a hydrocarbon group having 1 to 10 carbon atoms and $OA^1$ and $OA^2$ are the same or different and are an oxyalkylene group having 2 to 3 carbon atoms in the above formula (1).

3. The multibranched polyoxyalkylene compound according to claim 1, wherein $R^1$ is a methyl group and $OA^1$ and $OA^2$ are an oxyethylene group in the above formula (1).

4. The multibranched polyoxyalkylene compound according to claim 1, wherein m is the same or different and is 50 to 1000 in the above formula (1).

5. The multibranched polyoxyalkylene compound according to claim 1, wherein m is the same or different and is 100 to 800 in the above formula (1).

6. The multibranched polyoxyalkylene compound according to claim 1, wherein n is 0 in the above formula (1).

7. The multibranched polyoxyalkylene compound according to claim 1, wherein n is 1 to 1000 in the above formula (1).

8. The multibranched polyoxyalkylene compound according to claim 1, wherein n is 200 to 1000 in the above formula (1).

9. The multibranched polyoxyalkylene compound according to claim 1, wherein X is a functional group selected from the group consisting of an activated ester, a carbonate, an aldehyde, a thiol, a maleimide that may be substituted, a dithiopyridine, a sulfone, an amine, an oxyamine, a hydrazide, an α-haloacetyl, a carboxylic acid, a triple bond, and an azide in the above formula (1).

10. The multibranched polyoxyalkylene compound according to claim 1, wherein, in the above formula (1), X is a functional group selected from the group consisting of:

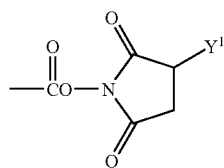 (a)

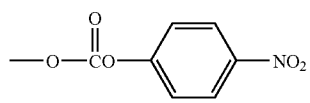 (b)

 (c)

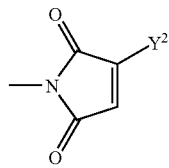 (d)

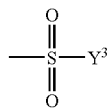 (e)

—COOH (f)

—SH (g)

 (h)

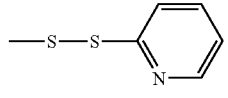 (i)

—C≡CH (j)

—NH$_2$ (k)

—O—NH$_2$ (l)

 (m)

—N$_3$ (n)

wherein $Y^1$ is a hydrogen atom or a sulfonyl group, $Y^2$ is a hydrogen atom or a hydrocarbon group having 1 to 3 carbon atoms, $Y^3$ is a hydrocarbon group having 1 to 10 carbon atoms that may contain a fluorine atom or an alkoxy having 1 to 3 carbon atoms that may be substituted with a fluorine atom, and $W^1$ is a halogen atom.

11. A multibranched polyoxyalkylene compound represented by the following formula (2):

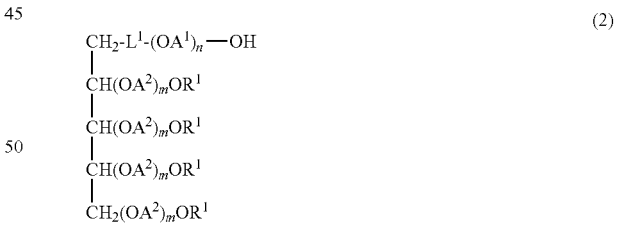

wherein $R^1$ is the same or different and is a hydrocarbon group having 1 to 24 carbon atoms, $OA^1$ and $OA^2$ are the same or different and are an oxyalkylene group having 2 to 4 carbon atoms, n and m are the same or different and are an average number of moles of the oxyalkylene group added, n represents 0 to 1000, m is the same or different and represents 10 to 1000, and $L^1$ represents a single bond, an alkylene group, or an alkylene group in which at least one bond selected from an ester bond, a urethane bond, an amide bond, an ether bond, a carbonate bond, and an amino is interposed.

12. A producing method of the multibranched polyoxyalkylene compound according to claim 1, which comprises the following steps (A2) to (A4):

Step (A2): a step of reacting a compound represented by the following formula (3):

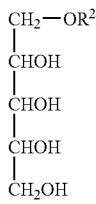
(3)

wherein $R^2$ is a hydrocarbon group having 1 to 24 carbon atoms, with an alkylene oxide to obtain a compound represented by the following formula (4):

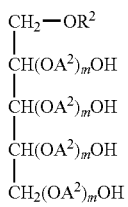
(4)

wherein $R^2$ is a hydrocarbon group having 1 to 24 carbon atoms, $OA^2$ is the same or different and is an oxyalkylene group having 2 to 4 carbon atoms, m is the same or different and is an average number of moles of the oxyalkylene group added, and m is the same or different and represents 10 to 1000, Step (A3): on the compound represented by the above formula (4), a step of etherifying the terminal hydroxyl group of the multibranched polyoxyalkylene and, after deprotection of $R^2$, introducing a group containing $L^1$ in the case where $L^1$ is not a single bond or an oxyalkylene in the case where n is 1 or more, thereby obtaining a compound represented by the following formula (2):

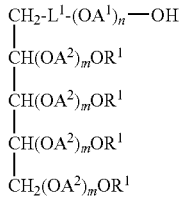
(2)

wherein $R^1$ is the same or different and is a hydrocarbon group having 1 to 24 carbon atoms, $OA^1$ and $OA^2$ is the same or different and is an oxyalkylene group having 2 to 4 carbon atoms, n and m is the same or different and is an average number of moles of the oxyalkylene group added, n represents 0 to 1000, m is the same or different and represent 10 to 1000, and $L^1$ represents a single bond, an alkylene group, or an alkylene group in which at least one bond selected from an ester bond, a urethane bond, an amide bond, an ether bond, a carbonate bond, and an amino is interposed, and Step (A4): a step of converting the hydroxyl group of the compound represented by the above formula (2) into -$L^2$-X where $L^2$ is the same or different and represents a single bond, an alkylene group, or an alkylene group in which at least one bond selected from an ester bond, a urethane bond, an amide bond, an ether bond, a carbonate bond, and an amino is interposed and X represents a functional group capable of reacting with an amino group, a mercapto group, an aldehyde group, a carboxyl group, a triple bond, or an azide group to form a chemical bond.

13. The producing method of the multibranched polyoxyalkylene compound, according to claim 12, wherein, as a compound represented by the following formula (3):

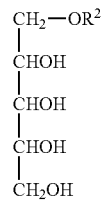
(3)

wherein $R^2$ is a hydrocarbon group having 1 to 24 carbon atoms, the compound obtained by the following step (B1) is used:

Step (B1): a step of protecting the hydroxyl group of a compound represented by the following formula (6):

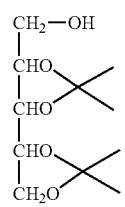
(6)

to obtain a compound represented by the following formula (5):

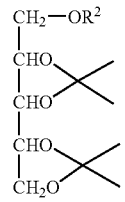
(5)

wherein $R^2$ is the same as above,
and subsequently obtaining a compound represented by the following formula (3):

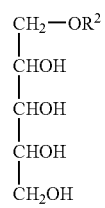
(3)

wherein $R^2$ is the same as above,
by acid hydrolysis.

14. The producing method of the multibranched polyoxyalkylene compound, according to claim 13, wherein, as a compound represented by the following formula (6):

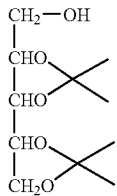
(6)

the compound obtained by the following steps (C1) and (C2) is used:

Step (C1): a step of ketalizing xylitol to obtain a mixture of compounds represented by the following formula (6) and the following formula (7):

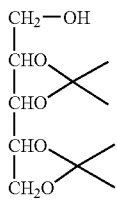
(6)

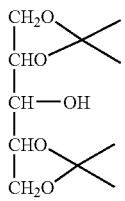
(7)

subsequently reacting the mixture with a silicon compound represented by the following formula (8):

(8)

wherein $W^2$ is a halogen atom or an alkyl sulfonate having 1 to 3 carbon atoms that may be substituted with 1 to 3 halogen atoms and $R^3$, $R^4$, and $R^5$ are a hydrocarbon group having 1 to 10 carbon atoms and are the same or different from one another in the same molecule, and a tertiary amine to obtain a mixture of compounds represented by the following formula (9):

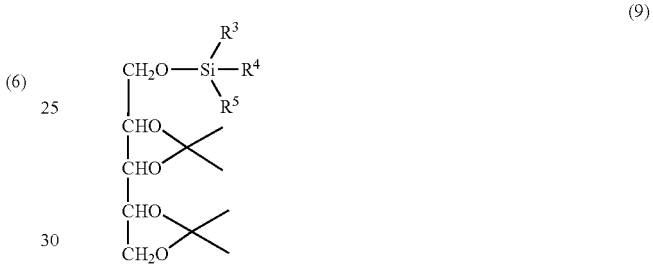
(9)

wherein $R^3$, $R^4$, and $R^5$ represent groups the same as above, and the compound represented by the above formula (7), and subsequently separating the compound represented by the above formula (9) from the mixture, Step (C2): a step of reacting the compound represented by the above formula (9) with a desilylation agent to obtain the compound represented by the above formula (6).

* * * * *